(12) United States Patent
Heinz

(10) Patent No.: US 8,845,652 B2
(45) Date of Patent: Sep. 30, 2014

(54) SURGICAL DRIVER

(75) Inventor: Eric S. Heinz, Memphis, TN (US)

(73) Assignee: Warsaw Orthopedic, Inc., Warsaw, IN (US)

(*) Notice: Subject to any disclaimer, the term of this patent is extended or adjusted under 35 U.S.C. 154(b) by 1659 days.

(21) Appl. No.: 11/679,694

(22) Filed: Feb. 27, 2007

(65) Prior Publication Data

US 2008/0243133 A1 Oct. 2, 2008

(51) Int. Cl.
*A61B 17/58* (2006.01)
*B25B 23/08* (2006.01)
*B25B 23/10* (2006.01)
*A61B 17/70* (2006.01)

(52) U.S. Cl.
CPC .............. *B25B 23/101* (2013.01); *B25B 23/08* (2013.01); *A61B 17/7038* (2013.01); *A61B 17/7037* (2013.01); *A61B 17/7082* (2013.01)
USPC ......................................................... 606/104

(58) Field of Classification Search
USPC .......................... 606/104, 99; 81/52, 451–458
See application file for complete search history.

(56) References Cited

U.S. PATENT DOCUMENTS

| | | | | |
|---|---|---|---|---|
| 772,912 | A * | 10/1904 | Allam | 81/451 |
| 2,248,054 | A * | 7/1941 | Becker | 81/457 |
| 2,292,657 | A * | 8/1942 | Priest | 81/453 |
| 2,472,103 | A * | 6/1949 | Giesen | 81/455 |
| 3,191,647 | A * | 6/1965 | Monnin | 81/475 |
| 3,244,208 | A * | 4/1966 | McKenzie | 81/453 |
| 5,207,127 | A * | 5/1993 | Nick | 81/54 |
| 5,458,030 | A * | 10/1995 | Betts | 81/451 |
| 5,591,212 | A | 1/1997 | Keimel | |
| 5,797,918 | A | 8/1998 | McGuire et al. | |
| 5,971,987 | A | 10/1999 | Huxel et al. | |
| 6,299,616 | B1 * | 10/2001 | Beger | 606/86 R |
| 6,415,693 | B1 | 7/2002 | Simon et al. | |
| 6,701,812 | B1 * | 3/2004 | Sawamura | 81/453 |
| 6,827,722 | B1 * | 12/2004 | Schoenefeld | 606/104 |
| 6,830,574 | B2 * | 12/2004 | Heckele et al. | 606/104 |
| 6,997,086 | B1 | 2/2006 | Graham | |
| 7,207,995 | B1 * | 4/2007 | Vandewalle | 606/104 |
| 2001/0021853 | A1 | 9/2001 | Heckele et al. | |
| 2004/0133207 | A1 * | 7/2004 | Abdou | 606/73 |
| 2004/0243139 | A1 | 12/2004 | Lewis et al. | |
| 2005/0033299 | A1 * | 2/2005 | Shluzas | 606/61 |
| 2005/0070918 | A1 | 3/2005 | Zwirnmann et al. | |
| 2005/0131408 | A1 | 6/2005 | Sicvol et al. | |
| 2005/0166725 | A1 * | 8/2005 | Chen | 81/451 |
| 2005/0216027 | A1 | 9/2005 | Suh et al. | |
| 2005/0228400 | A1 | 10/2005 | Chao et al. | |
| 2006/0069391 | A1 | 3/2006 | Jackson | |
| 2006/0075856 | A1 * | 4/2006 | Tilton | 81/452 |
| 2008/0140086 | A1 * | 6/2008 | Moore et al. | 606/104 |

* cited by examiner

Primary Examiner — Christian Sevilla

(57) ABSTRACT

Apparatus, methods, systems, and kits related to surgical procedures and instruments are disclosed. In one aspect, a method for securing a fixation device to a driver for use in a surgical procedure is disclosed. The method comprises engaging a first portion of the driver with the fixation device to limit rotational movement of the fixation device relative to the driver; and engaging a second portion of the driver with the fixation device to limit axial movement of the fixation device relative to the driver; wherein engaging the second portion of the driver with the fixation device comprises actuating an actuator of the driver to cause the second portion of the driver to move relative to the first portion of the driver. In other aspects, surgical drivers, surgical kits, and surgical procedures are disclosed.

33 Claims, 17 Drawing Sheets

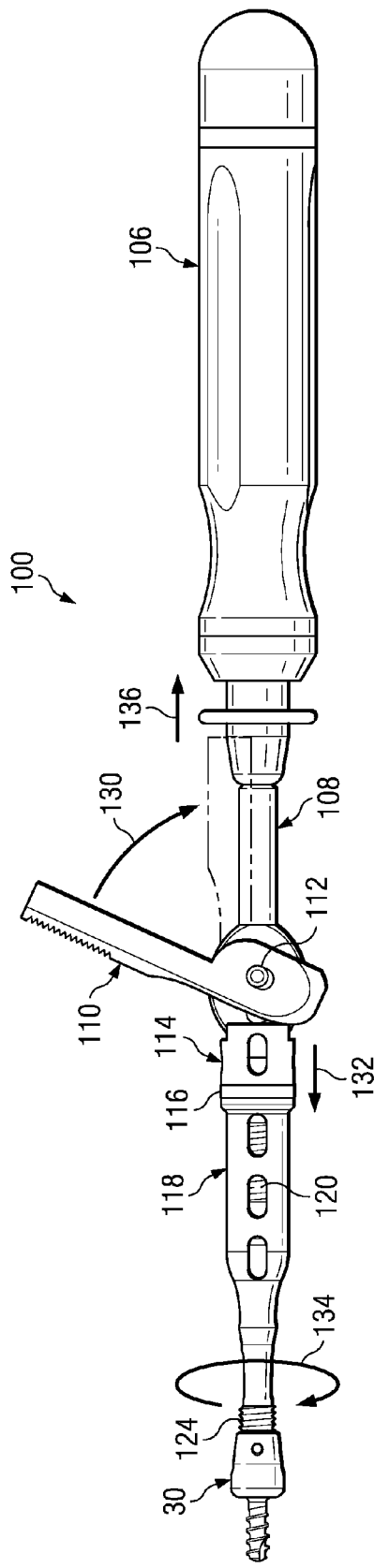
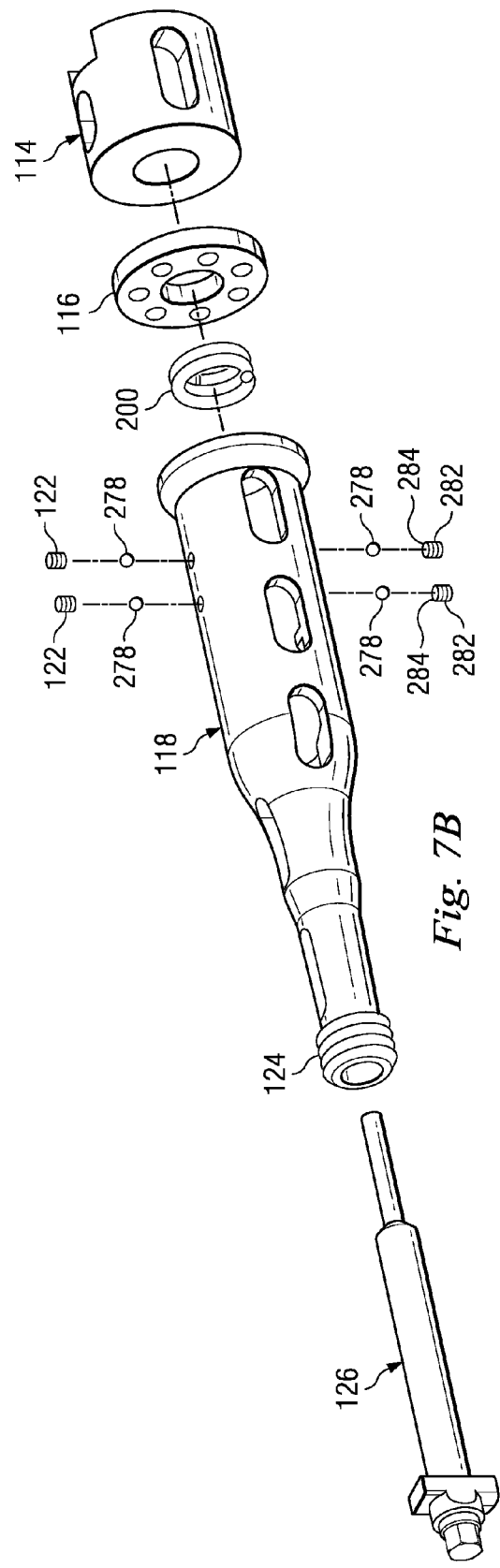
Fig. 6
Fig. 7B

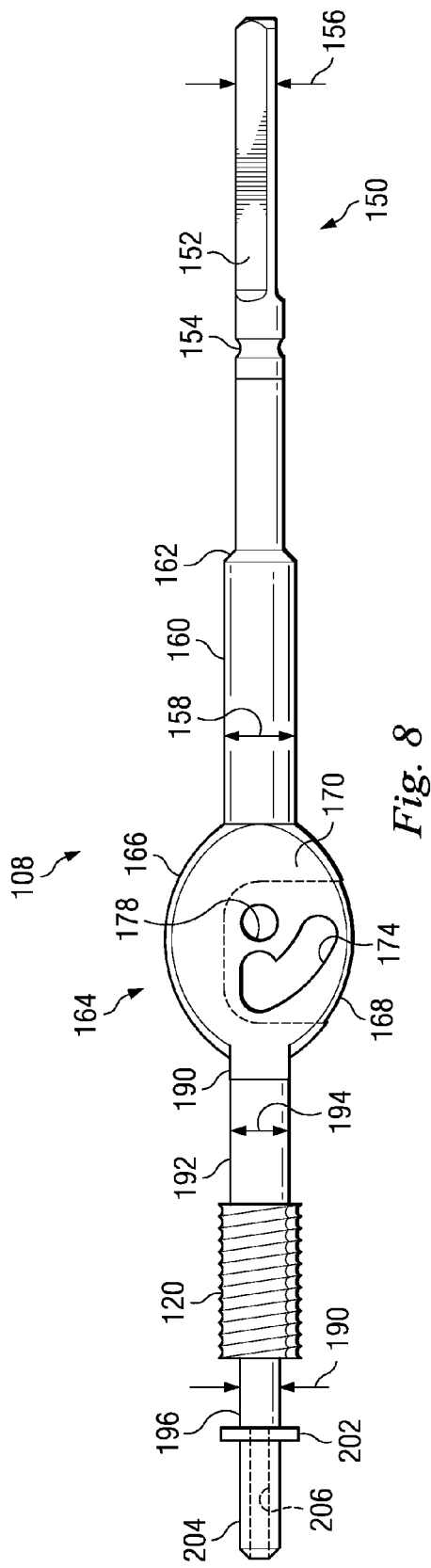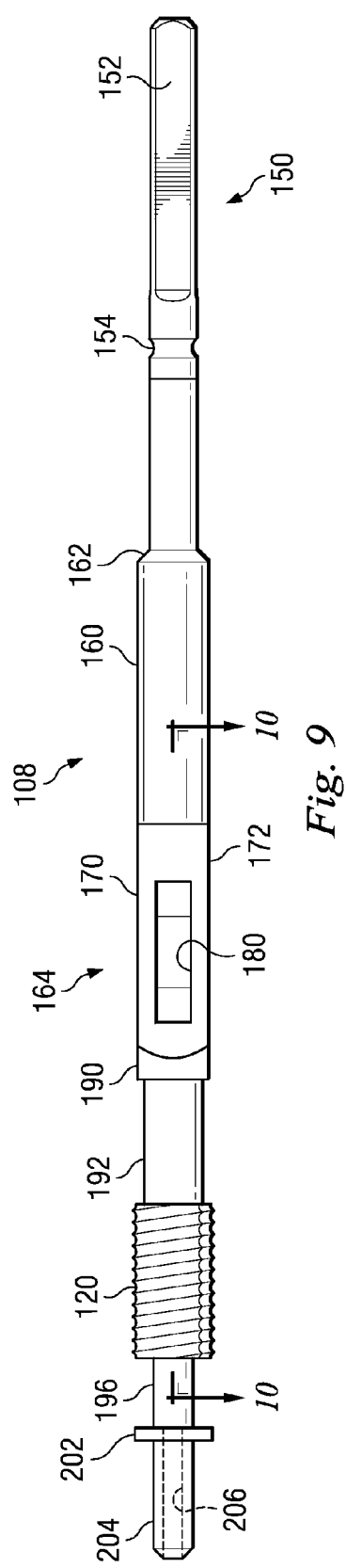

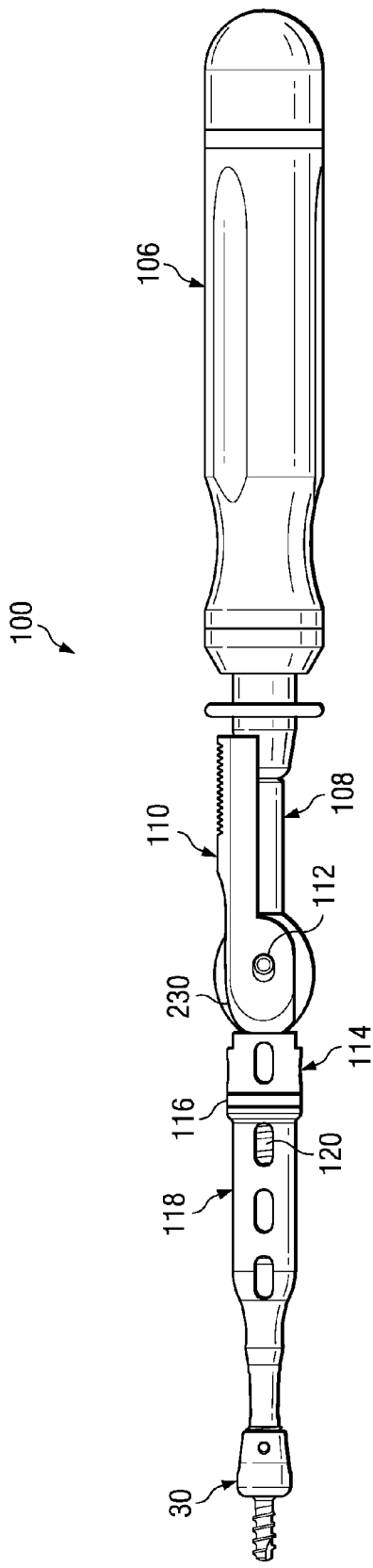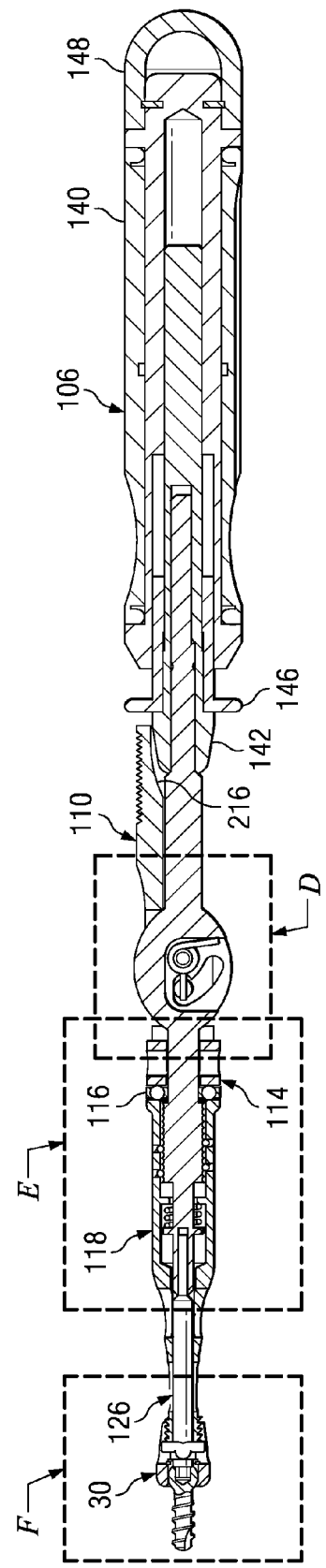

SURGICAL DRIVER

TECHNICAL FIELD

The present disclosure relates generally to devices, apparatus, systems, and methods for engaging an implant, and in some embodiments, to devices, apparatus, systems, kits, procedures, and methods for engaging and inserting a fixation device having a threaded head portion.

BACKGROUND

Although existing devices and methods for engaging fixation devices have been generally adequate for their intended purposes, they have not been entirely satisfactory in all respects.

SUMMARY

In one embodiment, a surgical driver is provided.

In another embodiment, a method for securing a fixation device to a driver for use in a surgical procedure is provided. The method comprises engaging a first portion of the driver with the fixation device to limit rotational movement of the fixation device relative to the driver; and engaging a second portion of the driver with the fixation device to limit axial movement of the fixation device relative to the driver. Engaging the second portion of the driver with the fixation device comprises actuating an actuator of the driver to cause the second portion of the driver to move relative to the first portion of the driver.

In another embodiment, a surgical driver is provided. The surgical driver comprises an elongated main shaft having a proximal portion, a distal portion, and a longitudinal axis extending therebetween. The distal portion of the main shaft is adapted to engage a first portion of an implant. A sleeve is movably connected to the main shaft such that the sleeve can rotate about the longitudinal axis of the main shaft as it translates along the longitudinal axis. The sleeve is adapted to threadingly engage a second portion of the implant. An actuator is also movably attached to the main shaft. The actuator is operative to move the sleeve relative to the main shaft between a first position for engaging the implant and a second position for releasing the implant.

In another embodiment, a surgical driver for engaging and implanting a fixation device is provided. The surgical driver comprises an elongated main shaft having a proximal portion, a distal portion, and a longitudinal axis extending therebetween. The distal portion of the main shaft is adapted to engage a first portion of the fixation device. A handle is attached to the proximal portion of the main shaft. An actuator is movably attached to the main shaft. The actuator is moveable between a first position for releasing the fixation device, a second position for engaging the fixation device, and a third position for locking the surgical driver to the fixation device. A spring biases the actuator towards the first position. A bushing is slidably attached to the main shaft and positioned adjacent the actuator. The bushing adapted to translate along the longitudinal axis when the actuator is moved among the first, second, and third positions. A sleeve is movably connected to a series of ball threads attached to the main shaft such that the sleeve rotates about the longitudinal axis of the main shaft as it translates along the longitudinal axis. The sleeve includes a threaded portion for engaging a second portion of the fixation device. A thrust bearing is positioned between the sleeve and the bushing to facilitate rotation of the sleeve relative to the bushing.

In another embodiment, a surgical kit is provided. The surgical kit comprises at least one fixation device and a driver. The driver has an elongated main shaft having a proximal portion, a distal portion, and a longitudinal axis extending therebetween. The distal portion of the main shaft is adapted to engage the at least one fixation device to limit relative rotational movement between the fixation device and the driver. A sleeve is movably connected to the main shaft. The sleeve is adapted to engage the at least one fixation device to limit relative axial movement between the fixation device and the driver. An actuator is movably attached to the main shaft. The actuator is adapted to move the sleeve relative to the main shaft between a first position for engaging the fixation device and a second position for releasing the fixation device.

In another embodiment, a surgical procedure is provided. The surgical procedure comprises providing an implant, providing a driver, engaging the driver to the implant, and implanting the implant. The provided driver comprises an elongated main shaft having a proximal portion, a distal portion, and a longitudinal axis extending therebetween. The distal portion of the main shaft is adapted to engage the implant to limit relative rotational movement between the implant and the driver. A sleeve is movably connected to the main shaft. The sleeve is adapted to engage the implant to limit relative axial movement between the implant and the driver. An actuator is movably attached to the main shaft. The actuator is adapted to move the sleeve relative to the main shaft between a first position for selectively engaging the implant and a second position for selectively releasing the implant.

Additional embodiments are included in the attached drawings and the description provided below.

BRIEF DESCRIPTION OF THE DRAWINGS

FIG. 6 is a diagrammatic side view of the driver of FIG. 5 illustrating motion paths of some of the components of the driver.

FIGS. 7A and 7B are diagrammatic, perspective exploded views of the driver of FIG. 5.

FIG. 8 is a diagrammatic side view of a main shaft of the driver of FIG. 5 according to at least one embodiment of the present disclosure.

FIG. 9 is a diagrammatic bottom view of the main shaft of FIG. 8.

FIG. 28 is a diagrammatic side view of the driver of FIG. 5 in a closed and unlocked position.

FIG. 29 is a diagrammatic, side cross-sectional view of the driver of FIG. 5 in the closed and unlocked position.

DETAILED DESCRIPTION

Figure 1:
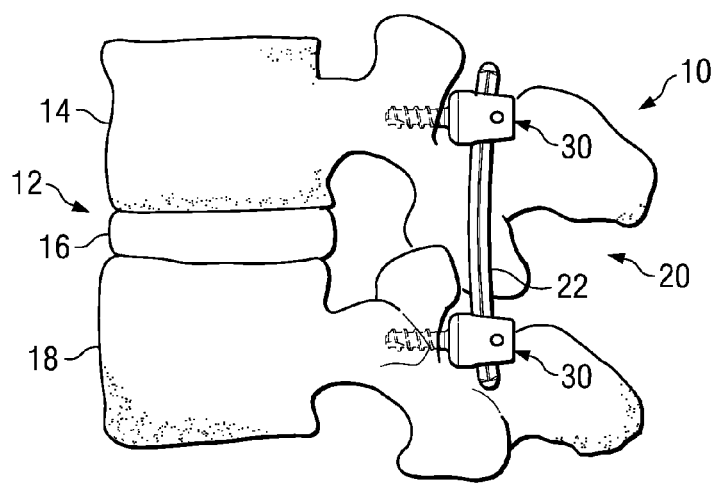
FIG. 1 is a diagrammatic side view of a vertebral motion segment that is at least partially supported by a spinal implant secured to the motion segment by a pair of fixation devices.

The present disclosure relates generally to devices, methods, and apparatus for inserting a fixation device, and more particularly, to devices for inserting fixation devices having a threaded head portion. For the purposes of promoting an understanding of the principles of the invention, reference will now be made to the specific embodiments, or examples, illustrated in the drawings. Though specific language will be used to describe the specific embodiments, it will nevertheless be understood that no limitation to the scope of the invention is intended. Any alterations and further modifications to the described embodiments, and any further applications of the principles of the invention as described herein are fully contemplated as would normally occur to one skilled in the art to which the invention relates.

Referring now to FIG. 1, shown therein is a diagrammatic side view of an arrangement 10 that includes a vertebral motion segment 12. The motion segment 12 includes a superior vertebra 14, an intervertebral disc 16, and an inferior vertebra 18. The motion segment 12 is at least partially supported by a spinal implant 20. The spinal implant 20 includes an elongated spinal prosthetic or spinal support member 22 and upper and lower fixation elements 30. The upper fixation element 30 secures the spinal support member 22 to the superior vertebra 14 and the lower fixation element 30 secures the spinal support member to the inferior vertebra 18.

Figure 2:
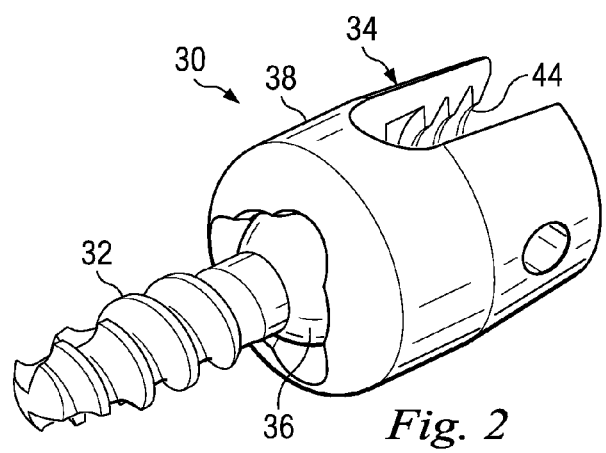
FIG. 2 is a diagrammatic perspective view of one embodiment of a fixation device for securing the spinal implant of FIG. 1.
Figure 3:
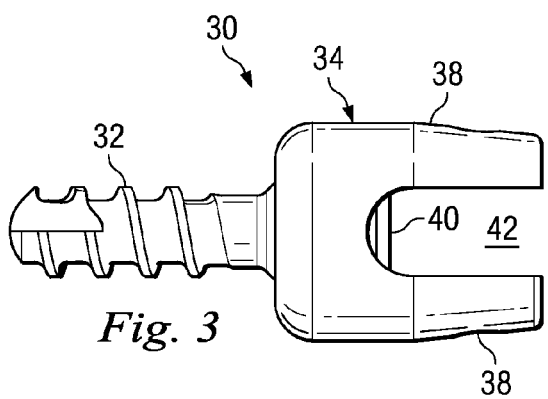
FIG. 3 is a diagrammatic top view of the fixation device of FIG. 2.
Figure 4:
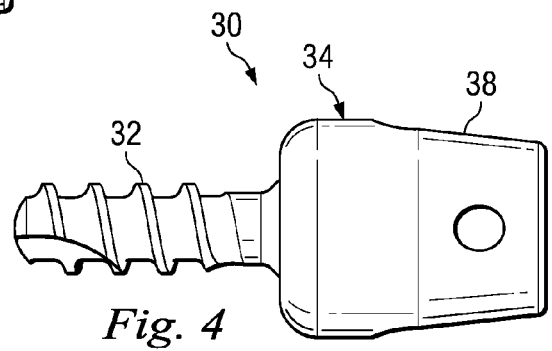
FIG. 4 is a diagrammatic side view of the fixation device of FIG. 2.

Referring now to FIG. 2-4, shown therein is one embodiment of the fixation devices 30 for securing an implant to a bone. FIG. 2 is a diagrammatic perspective view of the fixation device 30. FIG. 3 is a diagrammatic top view of the fixation device 30. FIG. 4 is a diagrammatic side view of the fixation device. The illustrated fixation device 30 is a multi-axial screw having a threaded portion 32 and a head portion 34. The threaded portion 32 is adapted for engaging bone. The head portion 34 comprises an inner head 36 that is integral with the threaded portion 32 and an outer sleeve portion 38. The inner head 36 and the threaded portion 32 are moveable with respect to the outer sleeve portion 38.

The head portion 34 is adapted to mate with a subsequently described driver to facilitate the insertion of the fixation device 30. Referring more specifically to FIG. 3, the inner head 36 includes an engagement mechanism 40 accessible through an opening 42 in the sleeve portion 38. In some embodiments, the engagement mechanism 40 is a recess adapted to mate with a driver. Thus, the engagement mechanism 40 may be a hexagonal recess, a single recess for mating with a flathead-type screwdriver, a cross-shaped recess for mating with a Phillips-head-type screwdriver, any geometrical recess, any other type of recess for mating with a driver, and combinations thereof. In other embodiments, the engagement mechanism 40 may be a projection for mating with a driver.

Referring more specifically to FIG. 2, the outer sleeve portion 38 of the head portion 34 includes a series of threaded recesses 44 disposed on opposite interior side portions thereof and adapted to mate with a threaded portion of a driver. In other embodiments, the outer sleeve portion 38 may have a threaded portion adapted to mate with a series of threaded recesses of a driver. In either embodiment, the outer sleeve portion 38 can be engaged with the driver via the threaded engagement. The combination of the threaded engagement with the driver and the engagement between the engagement mechanism 40 and the driver allows the fixation device 30 to be inserted without the user needing to hold the fixation device onto the driver.

The fixation device 30 is just one example of a fixation device for use with the present disclosure. Many other fixation devices and implants may be used as would be apparent to one skilled in the art. In general, the devices described below may be used with any type of fixation device or implant that is configured for threaded engagement with a driver. Reference to fixation device 30 will be made throughout this description in describing various embodiments of the present disclosure. This, however, is for purposes of clarity and illustration and is not a limitation on the types of fixation devices and implants that may be used in conjunction with the present disclosure.

Figure 5:
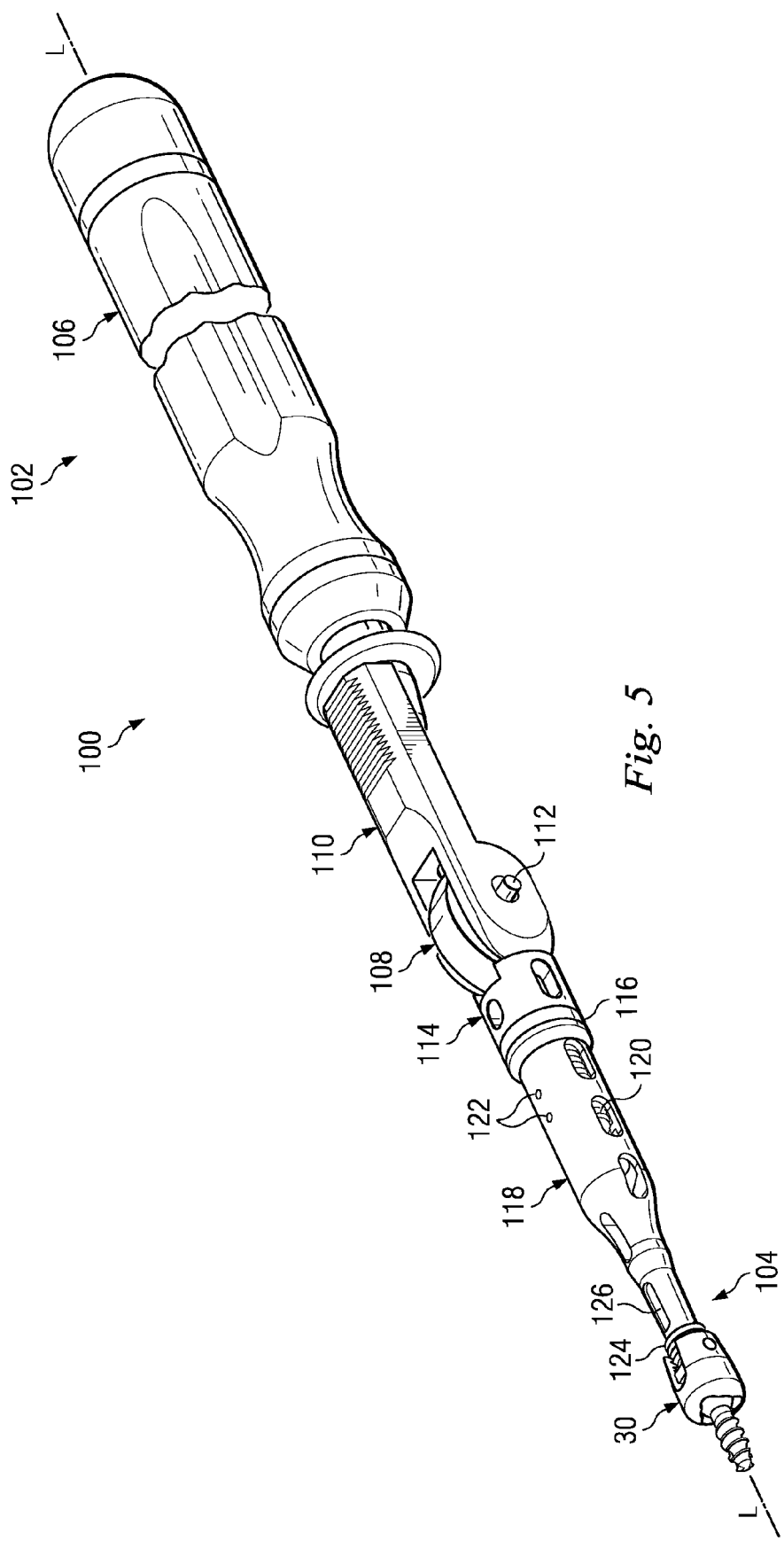
FIG. 5 is a diagrammatic perspective view of a driver that embodies aspects of the present disclosure.

Referring now to FIG. 5, shown therein is a diagrammatic perspective view of a driver 100 that embodies aspects of the present disclosure. The driver 100 is elongated and includes a proximal portion 102 and a distal portion 104. A longitudinal axis L extends substantially along the length of the driver 100. The distal portion 104 of the driver 100 is adapted to engage with a fixation device, such as the fixation device 30, as shown. As will be described in greater detail below, the driver 100 as illustrated in FIG. 5 is engaged with the fixation device 30 in a closed and locked position. The driver 100 includes a handle 106 that is attached to a main shaft 108 towards the proximal portion 102 of the driver. An actuator 110 is connected to the main shaft 108 about a pivot rod 112. A bushing 114 is positioned adjacent the actuator 110 distally along the main shaft 108. As described in more detail below, the bushing 114 is adapted to translate along the main shaft 108 parallel to the longitudinal axis L when the actuator 110 is actuated. A thrust bearing 116 is positioned adjacent the bushing 114 distally along the main shaft 108. The thrust bearing 116 is also adapted to translate along the main shaft 108 parallel to the longitudinal axis L when the actuator 110 is actuated.

A sleeve 118 is positioned adjacent the thrust bearing 116 distally along the main shaft 108. The sleeve 118 maintains two pairs of ball bearings (not visible in FIG. 5) in contact with a ball thread 120 of the main shaft 108. One of the two pairs of ball bearings is positioned below a pair of surface plugs 122. Using the interaction between the ball bearings and the ball thread 120, the sleeve 118 is adapted to translate along and rotate about the longitudinal axis L when the actuator 110 is actuated. The sleeve 118 also includes a threaded portion 124 for engaging with the threaded recesses 44 (see FIG. 2) of the fixation device 30. Extending partially within the sleeve 118 and connected to the main shaft 108 is an engagement shaft 126. The distal end of the engagement shaft 126 is adapted to mate with the engagement mechanism 40 (see FIG. 3) of the fixation device 30.

Referring now to FIG. 6, shown therein is a diagrammatic side view of the driver 100 illustrating motion paths of some of the components of the driver according to one aspect of the present disclosure. In particular, FIG. 6 illustrates the resultant motion of the sleeve 118 caused by depressing the actuator 110 as illustrated by path 130. As the actuator 110 is depressed along path 130, its distal end engages and leftwardly drives the bushing 114 distally along the main shaft 108, represented by path 132. The bushing 114, in turn, urges the thrust bearing 116 distally along the main shaft 108, which, in turn, urges the sleeve 118 distally along the main shaft. As the sleeve 118 translates distally along the main shaft 108, the ball bearings (not shown in FIG. 5) positioned between the sleeve and the ball thread 120 cause the sleeve to rotate about the main shaft as it translates. This rotation is represented by path 134. The translation and rotation of the sleeve 118 allows the sleeve to be threaded onto the fixation device 30 simply by depressing the actuator 110. Once the actuator 110 has been lowered or closed, the actuator can then be translated proximally along the main shaft 108, represented by path 136, to lock the actuator in the closed position.

Figure 7A:
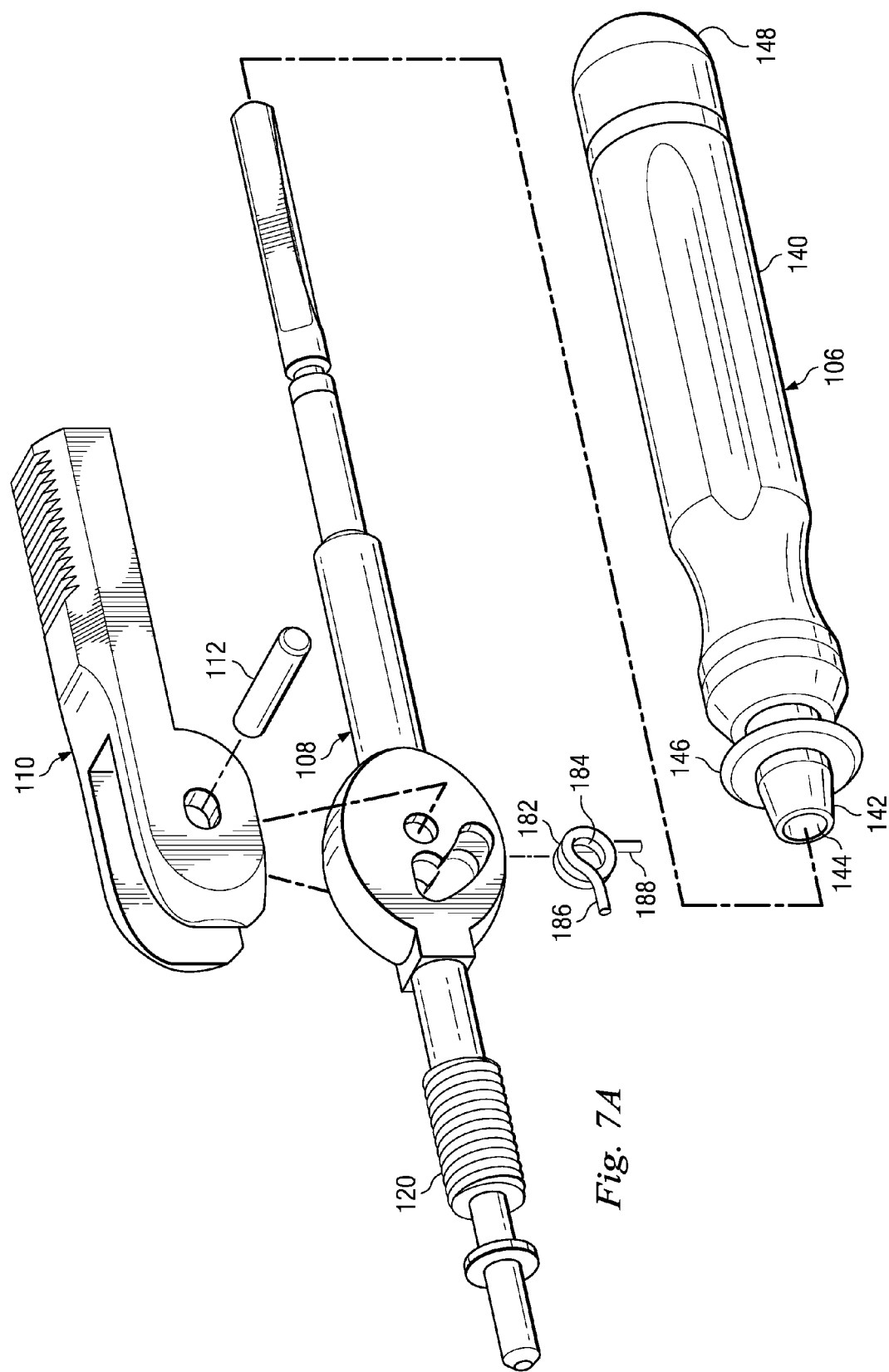

Referring now to FIGS. 7A and 7B, shown therein are diagrammatic, perspective exploded views of the driver 100 showing the various components of the driver. Referring first to FIG. 7A, the handle 106 is adapted to mate with a portion of the main shaft 108. In the illustrated embodiment, the handle 106 is modular. That is, the handle 106 is modular in that it may be used with multiple types surgical tools or drivers. The handle 106 includes a gripping portion 140 for grasping by a user. An engagement portion 142 extends at least partially within the gripping portion 140 and includes an opening 144 extending along its length to receive a proximal portion of the main shaft 108. The engagement portion 142 is adapted to selectively engage the handle 106 to the main shaft 108. In the illustrated embodiment, the engagement portion 142 translates distally relative to the gripping portion 140 to selectively engage the main shaft 108 and translates proximally relative to the gripping portion to disengage the main shaft. The engagement portion 142 includes an annular flange 146 for grasping by a user to facilitate translation of the engagement portion relative to the gripping portion 140 for selective engagement of the main shaft 108. Though a particular embodiment of the modular handle 106 has been described, it is understood that many other modular and non-modular handles may be used as part of the driver 100 as would be apparent to one skilled in the art. In some embodiments, the handle 106 may be permanently attached to and/or integral with the main shaft 108.

Figure 10:
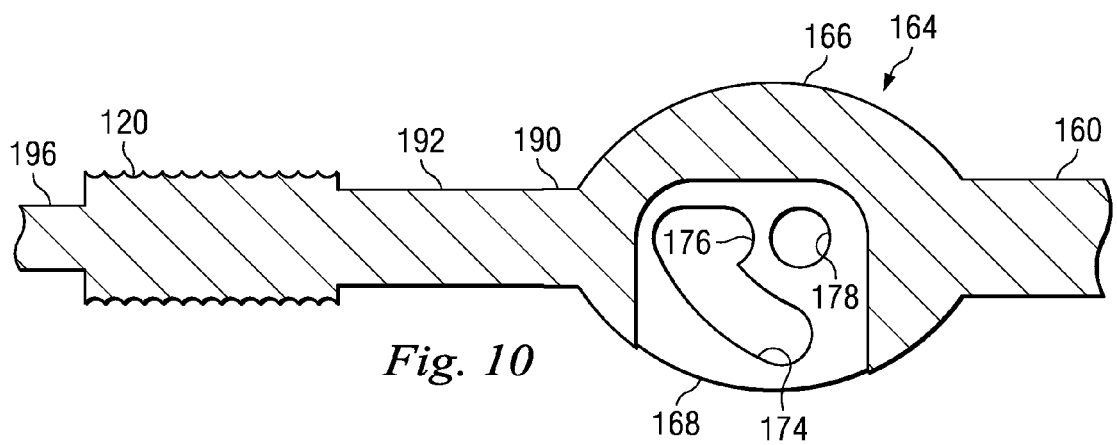
FIG. 10 is a diagrammatic cross-sectional view of the main shaft of FIGS. 8 and 9 taken along section line 10-10 of FIG. 9.

As shown in FIG. 7A, the driver 100 also includes the main shaft 108. Further details of the main shaft 108 are shown in FIGS. 8, 9, and 10. FIG. 8 is a diagrammatic side view of the main shaft 108. FIG. 9 is a diagrammatic bottom view of the main shaft 108. FIG. 10 is a diagrammatic cross-sectional view of the main shaft 108 taken along section line 10-10 of FIG. 9. Referring now to FIGS. 7A, 8, 9, and 10, the main shaft 108 includes a proximal portion 150. The proximal portion 150 is adapted for mating with the engagement portion 142 of the handle 106. In the illustrated embodiment, the proximal portion 150 includes a shaft portion 152 and an engagement feature 154. The size, shape, and length of the shaft portion 152 are adapted to mate with the opening 144 of the handle 106. In the illustrated embodiment, the shaft portion 152 comprises a tri-flat design. That is, the shaft portion 152 is comprised of three substantially planar surfaces arranged to form a substantially triangular-shaped shaft. However, in other embodiments the shaft portion 152 has other shapes and/or cross-sections, such as circular, cylindrical, square, pentagonal, hexagonal, other geometrical shapes, non-geometrical shapes, and combinations thereof.

In the illustrated embodiment, the engagement feature 154 is an annular recess adapted to mate with a projection, ball-bearing, or other protruding engagement mechanism (not shown) of the handle 106. In other embodiments, the engagement feature 154 may be non-annular in that it does not extend around the entire circumference of the proximal portion. Further, in some embodiments the engagement feature may comprise a projection, a recess, or combinations thereof. In the illustrated embodiment, the proximal portion 150 has a diameter 156 that is smaller than the diameter 158 of a central portion 160 of the main shaft 108. A taper or transition 162 serves as the transition between the proximal portion 150 and the central portion 160. In addition, the transition 162 may function as a stop to limit the positioning of the handle 106 along the length of the main shaft 108.

Adjacent the central portion 160, the main shaft 108 also includes an actuator interface 164. The interface 164 is adapted to receive the actuator 110 and its related components. The interface 164 serves to coordinate the movements of the actuator 110 and its related components with the other parts of the driver 100. In the illustrated embodiment, the interface 164 is oblong when viewed from the side with substantially convex upper and lower surfaces 166 and 168. The interface 164 has substantially planar side surfaces 170 and 172, as best seen in FIG. 9. Referring more particularly to FIGS. 8 and 10, the interface 164 includes an opening 174 that extends laterally through the interface and through each of the surfaces 170 and 172. The opening 174 serves as a guide for a portion of the actuator 110. The opening 174 is curved along its length and includes a detent 176 adjacent one end. The detent 176 serves as a locking mechanism for the actuator 110. The interface 164 also includes an opening 178 that extends laterally through the interface and through each of the surfaces 170 and 172. The opening 178 is adapted to receive the pivot rod 112 shown in FIG. 7A.

Referring more specifically to FIG. 9, the interface 164 also includes an opening 180 that extends through the bottom surface 168. In the illustrated embodiment, the opening 180 is substantially rectangular and is adapted to receive a torsion spring 182, shown in FIG. 7A. Referring to FIG. 7A, the torsion spring 182 is adapted to bias the actuator 110 to a predetermined position, such as an open position, a closed position, and positions in between. In some embodiments, the torsion spring 182 may be adapted to mate with the pivot rod 112. For example, in some embodiments the torsion spring 182 includes a central opening 184 adapted to receive the pivot rod 112. The torsion spring 182 may be connected to the main shaft 108 of the driver 100 by having pivot rod 112 pass through its opening 184 and also through the opening 178 of the actuator interface 164. The torsion spring 182 also includes leads 186 and 188. The lead 186 is adapted to mate with an opening in a portion of the actuator 110, as described more fully below.

Referring again to FIGS. 7A, 8, 9, and 10, the interface 164 also includes a distal portion 190. The distal portion 190 is adapted to mate with the bushing 114. In particular the distal portion 190 is adapted to mate the bushing 114 so as to limit or prevent rotational movement of the bushing relative to the longitudinal axis L of the driver 100. In the illustrated embodiment, the distal portion 190 includes four substantially planar surfaces. The distal portion 190 has a substantially equal height and width in the illustrated embodiment. In particular, the height and width of the distal portion 190 is substantially equal to the diameter 158 of the central portion 160. In other embodiments, the distal portion may take on numerous other shapes and features to limit or prevent rotational movement of the bushing 114. Similarly, in other embodiments the distal portion 190 may have a different height and/or width.

Extending from the distal portion 190 of the interface 164 is an intermediate shaft 192. In the illustrated embodiment, the intermediate shaft 192 has a diameter 194 that is substantially equal to or less than the height and/or width of the distal portion 190. Thus, in the illustrated embodiment the diameter 194 of the intermediate shaft 192 is substantially equal to or less than the diameter 158 of the central portion 160. Positioned adjacent the intermediate shaft 192 is the ball thread 120. The ball thread 120 is adapted interface with a set of balls to incite rotation upon the sleeve 118 as the sleeve is urged distally along the main shaft 108. Thus, the diameter of the ball thread 120 may be sized to match the size of the set of balls being utilized. Further, the pitch of the ball thread 120 may be selected to create a desired amount of rotation (e.g., number of turns) of the sleeve 118 per unit of linear translation of the sleeve. Thus, in some embodiments the ball thread 120 is adapted to incite approximately 4 turns of the sleeve 118 upon the sleeve being translated by moving the actuator from the open position to the closed position. In other embodiments, the ball thread 120 is adapted to incite other numbers of turns, including fractions of a turn. For example, in some embodiments the ball thread 120 is adapted for use with quarter-turn fixation devices.

Extending distally from the ball thread 120 is a shaft 196. In the illustrated embodiment, the shaft 196 has a diameter 198 that is less than the diameters 158 and 194 of the central portion and the intermediate shaft 192, respectively. In particular, the diameter 198 of the shaft 198 is sized such that a spring 200, as shown in FIG. 7B, may be positioned around the shaft 198. Referring to FIG. 7B, the spring 200 may be a coiled spring (as shown), a Belleville washer, a series of Belleville washers, or other mechanism for producing a force to urge components of the driver 100 towards a particular position. The spring 200 may bias components of the driver 100 towards an open position, a closed position, and positions in between. To achieve such a bias, the spring 200 is adapted to interact with other components of the driver.

Referring again to FIGS. 7A, 8, 9, and 10, in the illustrated embodiment the spring 200 is adapted to interact with an annular flange 202 of the main shaft 108 and a portion of the sleeve 118 to bias the driver 100 towards an open position. In other embodiments, the spring 200 may be adapted to interact with other components of the driver 100. Further, in other embodiments the annular flange 202 may be replaced with an alternative feature for interacting with the spring, such as a non-annular flange, a projection, or other structure. The main shaft 108 also includes a distal portion 204 extending beyond the annular flange 202. The distal portion 204 is adapted to mate with the engagement shaft 126. To that end, the distal portion 204 includes an opening 206 extending therein for receiving a portion of the engagement shaft 126. In the illustrated embodiment, the opening 206 is sized and shaped to mate with the engagement shaft 126. In some embodiments, the opening 206 includes additional features, such as projections, recesses, and/or other structures, adapted to facilitate secure engagement between the distal portion 204 and the engagement shaft 126. In some embodiments, the engagement shaft 126 and the distal portion 204 are welded together.

Figure 11:
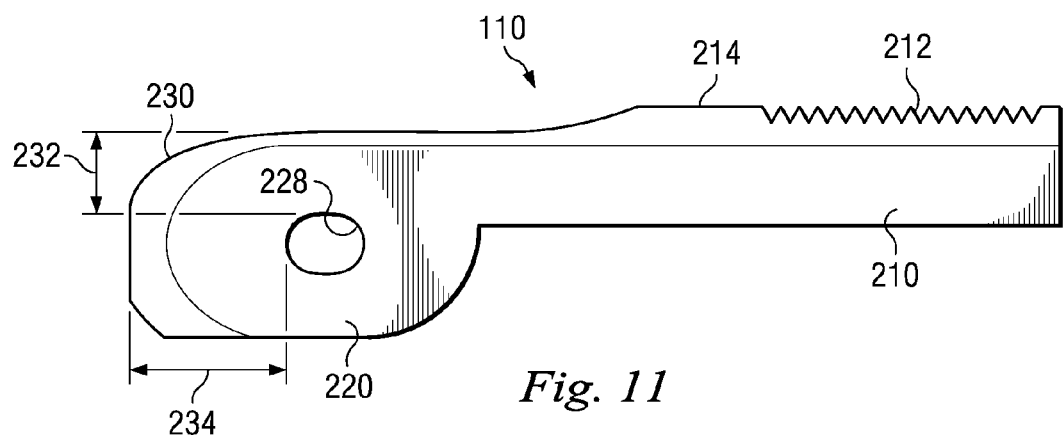
FIG. 11 is a diagrammatic side view of an actuator of the driver of FIG. 5 according to at least one embodiment of the present disclosure.
Figure 12:
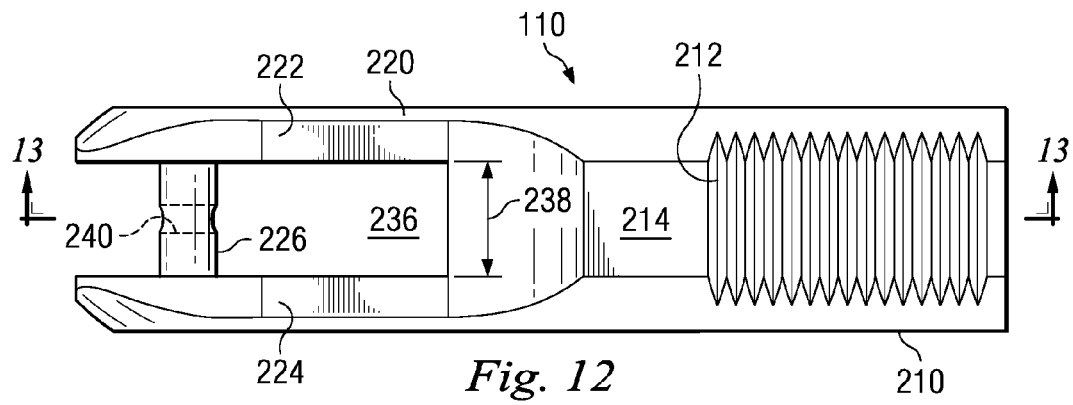
FIG. 12 is a diagrammatic top view of the actuator of FIG. 11.
Figure 13:
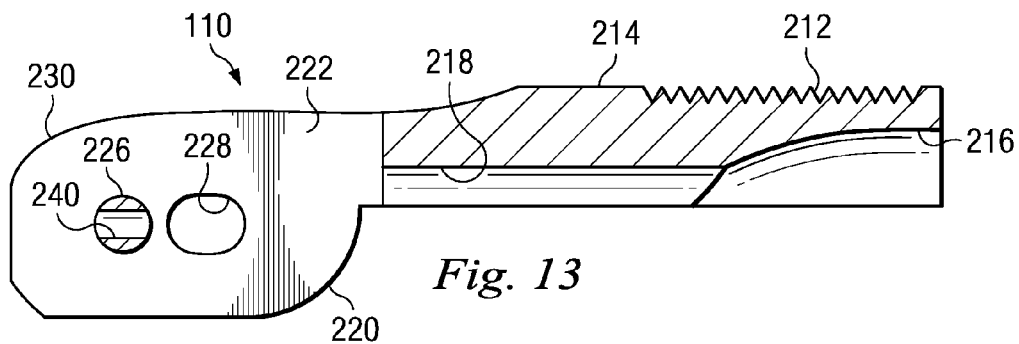
FIG. 13 is a diagrammatic cross-sectional view of the actuator of FIGS. 11 and 12 taken along section line 13-13 of FIG. 12.

Referring again to FIG. 7A, the driver 100 also includes the actuator 110. Further details of the actuator 110 are shown in FIGS. 11, 12, and 13. FIG. 11 is a diagrammatic side view of the actuator 110. FIG. 12 is a diagrammatic top view of the actuator 110. FIG. 13 is a diagrammatic cross-sectional view of the actuator 110 taken along section line 13-13. Referring now to FIGS. 7A, 11, 12, and 13, the actuator 110 includes a gripping portion 210 adjacent one end. The gripping portion 210 includes a textured area 212 on an upper surface 214. In the illustrated embodiment, the textured area 212 comprises a series of projections and recesses. The textured area 212 is adapted to provide a non-slip or limited-slip grip for a user of the driver 100. Numerous other textures or treatments may be used to enhance the grip of the gripping portion 210 besides the series of projections and recesses. For example, in other embodiments the textured area 212 may be roughened, knurled, etched, coated, or otherwise treated to enhance the grip of the gripping portion 210. In some embodiments, the gripping portion 210 is sized and/or shaped for interaction with a user's hand. For example, in some embodiments the actuator 110 is a thumb lever that may be depressed by the user's thumb.

Referring more specifically to FIG. 13, in the illustrated embodiment the gripping portion 210 also includes a recess 216 at least partially underneath the textured area 212. The recess 216 is adapted to substantially match the contours of the engagement portion 142 of the handle 106 such that when the actuator 110 is moved towards a closed position the gripping portion 210 does not inhibit the actuator from reaching the closed position by hitting the engagement portion of the handle. Similarly, the actuator 110 includes a recess 218 that is adapted to substantially match the contours of the central portion 160 of the main shaft 108 such that when the actuator 110 is moved towards a closed position the gripping portion 210 does not inhibit the actuator from reaching the closed position by hitting the central portion of the main shaft. In other embodiments, the recesses 216 and 218 do not substantially match the contours of the handle 106 and the main shaft 108, but are simply shaped so as not to interfere with the moving of the actuator between positions.

Referring again to FIGS. 7A, 11, 12, and 13, the actuator 110 also includes an interface portion 220. The interface portion 220 is adapted to interact with the pivot rod 112, the bushing 114, the actuator interface 164 of the main shaft 108, and the spring 182. The interface portion 220 is a bifurcated configuration and includes a pair of side extensions 222 and 224 and a cross member 226 extending therebetween. Openings 228 extend laterally through the extensions 222 and 224. The openings 228 are adapted to receive opposite ends of the pivot rod 112. The actuator 110 is adapted to rotate about the opening 228 and the pivot rod 112. In the illustrated embodiment, the openings 228 are elongated such that each opening's width is greater than its height when viewed from the side, as in FIGS. 11 and 13. In particular, the height of each opening 228 is substantially equal to or greater than the diameter of the pivot rod 220 and the width of each opening 228 is greater than the diameter of the pivot rod 220. The increased length of the width of the openings 228 allows the actuator 110 to translate along the longitudinal axis L of the driver 100 to a locked position when in the closed position.

Referring more specifically to FIG. 11, the interface portion 220 also includes a cam surface 230. The cam surface 230 is adapted to interface with the bushing 114. In particular, the cam surface 230 of the interface portion 220 is adapted to urge the bushing 114 distally along the longitudinal axis L of the driver as the actuator 110 is moved from an open position towards a closed position. The urging of the bushing 114 is caused by the increased radius or thickness of the interface portion 220 between the opening 228 and the cam surface 230 as the actuator 110 moves from an open position towards a closed position. In a fully opened position, the interface portion 220 has a thickness 232 between the opening 228 and the cam surface 230. In a fully closed position, the interface portion 220 has a thickness 234, greater than the thickness 232, between the opening 228 and the cam surface 230. The difference between the thicknesses 232 and 234 represents how far the bushing 114 will be pushed along the longitudinal axis L of the driver 100 when the actuator 110 is moved from the fully open position to the fully closed position. This, in turn, represents how far the sleeve 118 will be translated along the longitudinal axis L. Thus, the desired amount of translational movement for the sleeve 118 can be calibrated by specifying the difference in the thicknesses 232 and 234. In some embodiments, the difference in the thicknesses 232 and 234 is between about 0.5 mm and 6 mm. A difference of approximately 0.5 mm may be appropriate for use with a quarter-turn locking mechanism on a cervical screw. A difference of approximately 6 mm may be appropriate for use with a buttress-thread locking mechanism on a lumbar screw.

Referring more specifically to FIGS. 12 and 13, the interface portion 220 also includes the side extensions 222 and 224 and the cross member 226 extending therebetween. The extensions 222 and 224 are separated by a gap 236 having a width 238. In the illustrated embodiment, the width 238 is substantially equal to or larger than the width of the actuator interface 164 of the main shaft 108 such that at least a portion of the actuator interface may be positioned within the gap 236. The cross member 226 extends across the gap 236 between the extensions 222 and 224. The cross member 226 includes an opening 240 extending substantially transverse to the length of the cross member. In the illustrated embodiment, the opening 240 is adapted to receive the lead 186 of the spring 182 (see FIG. 7A). Further, in the illustrated embodiment the cross member 226 is substantially cylindrical with a diameter substantially equal to or less than a width of the opening 174 of the actuator interface 164 of the main shaft 108 such that the cross member may travel within and be guided by the opening 174. Further, the cross member 226 is adapted to engage the detent 176 of the opening 174 to lock the actuator 110 in a closed position.

Figure 14:
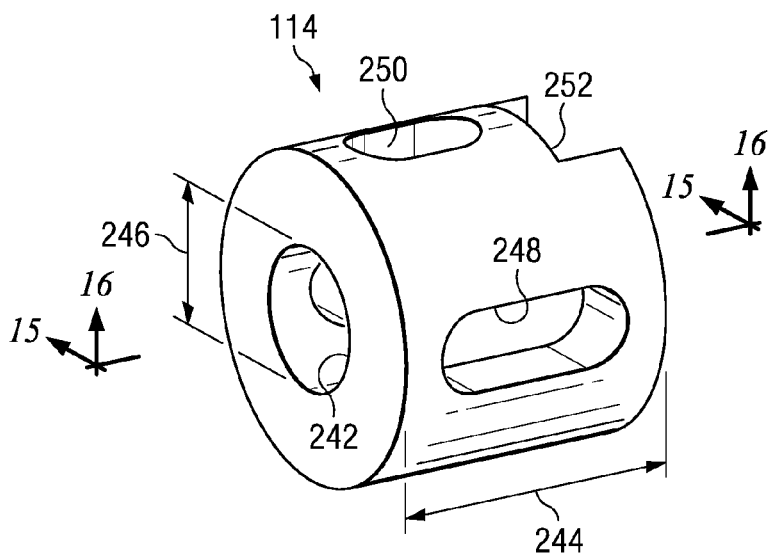
FIG. 14 is a diagrammatic perspective view of a bushing of the driver of FIG. 5 according to at least one embodiment of the present disclosure.
Figure 15:
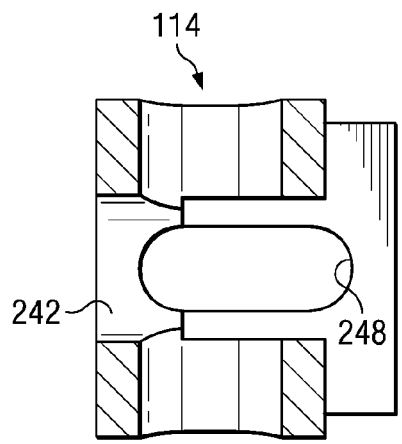
FIG. 15 is a diagrammatic cross-sectional view of the bushing of FIG. 14 taken along section line 15-15 of FIG. 14.
Figure 16:
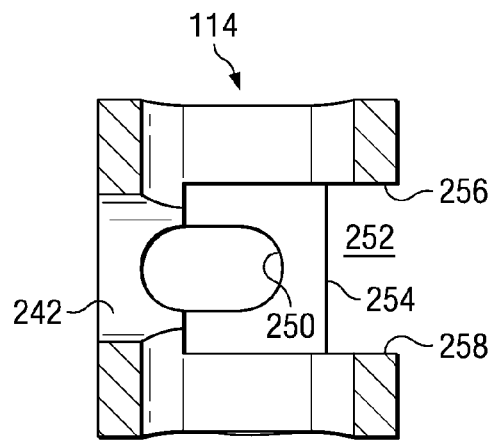
FIG. 16 is a diagrammatic cross-sectional view of the bushing of FIG. 14 taken along section line 16-16 of FIG. 14.

Referring now to FIG. 7B, the driver 100 also includes the bushing 114. Further details of the bushing 114 are shown in FIGS. 14, 15, and 16. FIG. 14 is a diagrammatic side view of the bushing 114. FIG. 15 is a diagrammatic cross-sectional view of the bushing 114 taken along section line 15-15 of FIG. 14. FIG. 16 is a diagrammatic cross-sectional view of the bushing 114 taken along section line 16-16 of FIG. 14. Referring now to FIGS. 7B, 14, 15, and 16, the bushing 114 includes an opening 242 extending substantially along its length 244. The opening 242 has a diameter 246 substantially equal to or greater than the diameter 194 of the intermediate shaft 192 such that the bushing 114 may be positioned around and translate along the intermediate shaft 192. An opening 248 extends substantially through the bushing 114 in a lateral direction as viewed in FIG. 14. An opening 250 extends substantially through the bushing 114 in a vertical direction as viewed in FIG. 14. The openings 248 and 250 are positioned and adapted to facilitate cleaning of the driver 100. For example, the openings 248 and 250 may facilitate removal of blood and/or tissue from the driver. The openings 248 and 250 may help to facilitate sanitizing of the driver 100 through autoclaving, chemical cleaning, or other methods such that the driver may be used in multiple surgical procedures.

Referring more specifically to FIGS. 14 and 16, the bushing 114 also includes a recess 252. The recess 252 is adapted to mate with the distal portion 190 of the main shaft 108. In that regard, the recess 252 includes three substantially planar walls: a back wall 254 and a pair of sidewalls 256 and 258. The walls 254, 256, and 258 are adapted to mate with the substantially planar surfaces of the distal portion 190 of the main shaft 108 to limit or prevent rotational movement of the bushing 114 relative to the longitudinal axis L of the driver. In other embodiments, the recess 252 may have other shapes and/or features, including projections, to prevent rotational movement of the bushing 114. Further, in some embodiments the bushing 114 may engage other portions of the main shaft 108 to limit rotational movement of the bushing. For example, in one embodiment a projection of the bushing 114 may engage a linear recess in the intermediate shaft 192 to prevent rotation of the bushing. Numerous other combinations of structures may be utilized to prevent and/or limit the rotation of the bushing 114.

Figure 17:
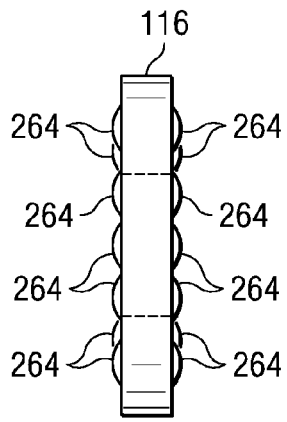
FIG. 17 is a diagrammatic side view of a thrust bearing of the driver of FIG. 5 according to at least one embodiment of the present disclosure.
Figure 18:
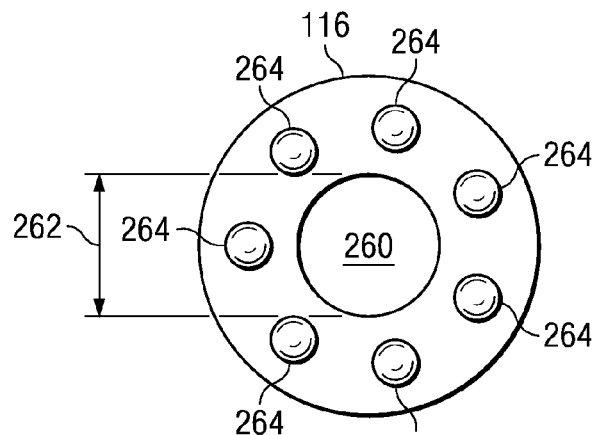
FIG. 18 is a diagrammatic end view of the thrust bearing of FIG. 17.

Referring again to FIG. 7B, the driver 100 also includes the thrust bearing 116. Further details of the thrust bearing 116 are shown in FIGS. 17 and 18. FIG. 17 is a diagrammatic side view of the thrust bearing 116. FIG. 18 is a diagrammatic end view of the thrust bearing 116. Referring now to FIGS. 7B, 17, and 18, the thrust bearing 116 includes a central opening 260 extending axially therethrough. The opening 260 has a diameter 262 substantially equal to or greater than the diameter 194 of the intermediate shaft 192 such that the thrust bearing 116 may be positioned around and translate along the intermediate shaft 192. The thrust bearing 116 is adapted to facilitate the rotational movement of the sleeve 118 in combination with the translational movement of the bushing 114. To that end, the thrust bearing 116 includes a plurality of ball bearings 264. In the illustrated embodiment, the thrust bearing 116 includes seven ball bearings 264 equally spaced about the circumference of the thrust bearing. In other embodiments, the thrust bearing 116 may include more or less ball bearings 264. The ball bearings 264 are adapted to movingly engage a surface of the bushing 114 and a surface of the sleeve 118. The ball bearings 264 serve to provide a low-friction interface between the bushing 114 and the sleeve 118. In this manner, the friction between the bushing 114 and the sleeve 118 is minimized to allow the sleeve to rotate with minimal resistance as it translates along the longitudinal axis L of the driver 100.

Figure 19:
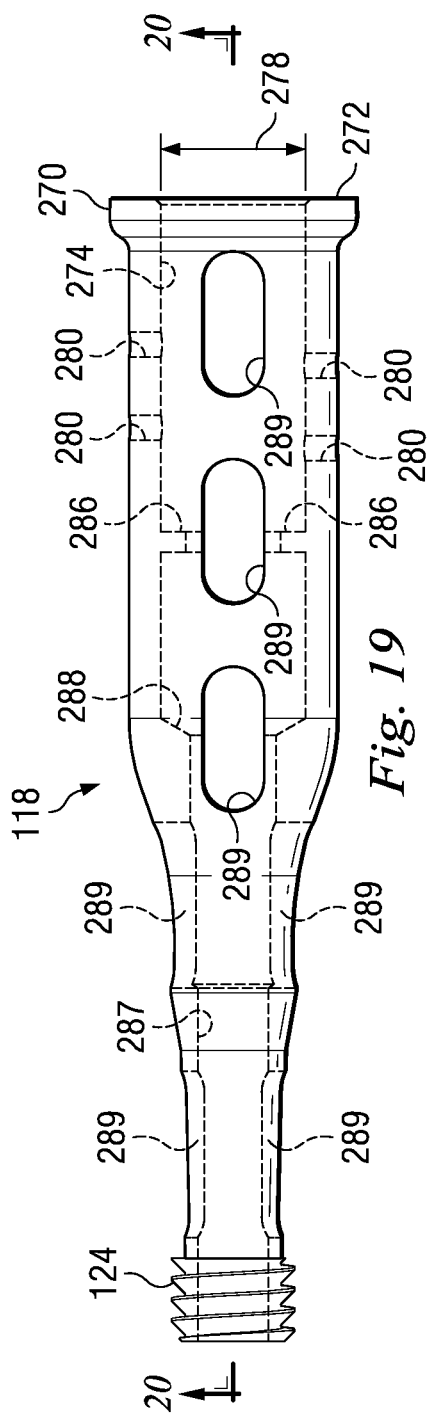
FIG. 19 is a diagrammatic side view of a sleeve of the driver of FIG. 5 according to at least one embodiment of the present disclosure.
Figure 20:
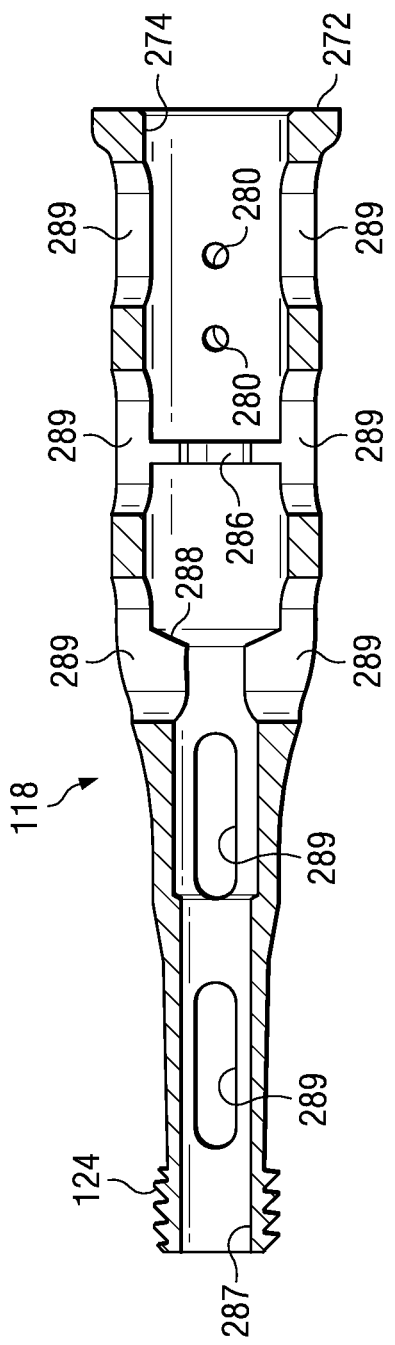
FIG. 20 is a diagrammatic cross-sectional view of the sleeve of FIG. 19 taken along section line 20-20 of FIG. 19.

Referring again to FIG. 7B, the driver 100 also includes the sleeve 118. Further details of the sleeve 118 are shown in FIGS. 19 and 20. FIG. 19 is a diagrammatic side view of the sleeve 118. FIG. 20 is a diagrammatic cross-sectional view of the sleeve 118 taken along section line 20-20 of FIG. 19. Referring now to FIGS. 7B, 19, and 20, the sleeve 118 includes a proximal portion 270. The proximal portion 270 is adapted to interface with the thrust bearing 216 and, in that regard, includes an annular surface 272 for movingly engaging the ball bearings 264 of the thrust bearing 116. The proximal portion 270 also includes an opening 274 extending therethrough. The opening 274 has a diameter 276 that is substantially equal to or greater than the diameter of the ball thread 120 such that the proximal portion 270 may be positioned around the ball thread.

The sleeve 118 is adapted to interface the ball thread 120 via a plurality of balls 278. To that end, the sleeve 118 includes a plurality of openings 280 adapted to receive the balls 278. The openings 280 have a diameter substantially equal to or greater than the balls 278. The plurality of balls 278 are secured within the plurality of openings 280 by plugs 122 and 282. The plugs 282 include a recess 284. In the current embodiment the recess 284 is at least partially spherical. In some embodiments, the recess 284 may be substantially semi-spherical. The recess 284 is adapted to allow the balls 278 to roll along and follow the pitch of the ball thread 120 causing the sleeve 118 to rotate. In some embodiments, the balls 278 and/or the recess 284 are coated or otherwise treated to reduce the friction between the balls and the recesses. The plugs 122 have similar recesses (not shown) to those described with respect to plugs 282. The plugs 122 and 282 may be welded, glued, press-fit, or otherwise secured into the openings 280 of the sleeve 118.

Within the opening 274, the sleeve 118 also includes a pair of flanges 286. The flanges 286 are adapted to interface with the spring 200. In particular, the flanges 286 serve as a stop for one end of the spring 200. The annular flange 202 of the main shaft 108 serves as the stop for the opposite end of the spring 200. In the illustrated embodiment, the spring 200 urges the flanges 286 away from the flange 202. That is, the spring 200 biases the driver 100 towards an open position. The opening 274 tapers into an opening 287 with a reduced diameter via a transition 288. The opening 287 is sized and shaped to receive at least a portion of the engagement shaft 126.

The sleeve 118 also includes a plurality of openings 289, as shown. The openings 289 are sized, shaped, and positioned to facilitate cleaning of the driver 100. For example, the openings 289 may facilitate removal of blood and/or tissue from the driver 100. The openings 289 may help to facilitate sanitizing of the driver 100 through autoclaving, chemical cleaning, or other methods such that the driver may be used in multiple surgical procedures. Each of the openings 289 may have a different size and/or shape. In some embodiments at least one of the openings 289 is utilized in connecting the engagement shaft 126 to the main shaft 108. For example, in some embodiments the engagement shaft 126 and the main shaft 108 are welded together and at least one of the openings 289 may be utilized. In that regard, at least one of the openings 289 may serve as a window to the junction of the engagement shaft 126 and the distal portion 204 of the main shaft 108 that can be accessed by a welding instrument.

Figure 21:
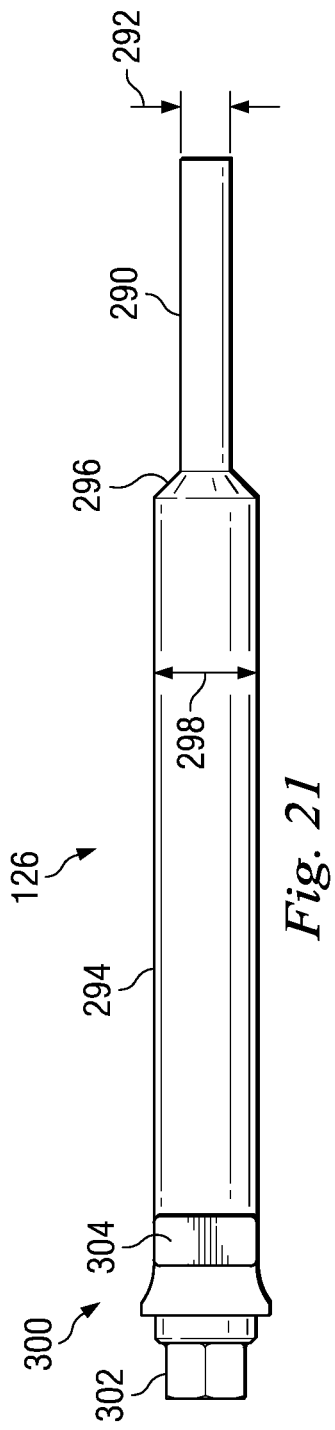
FIG. 21 is a diagrammatic side view of an engagement shaft of the driver of FIG. 5 according to at least one embodiment of the present disclosure.
Figure 22:
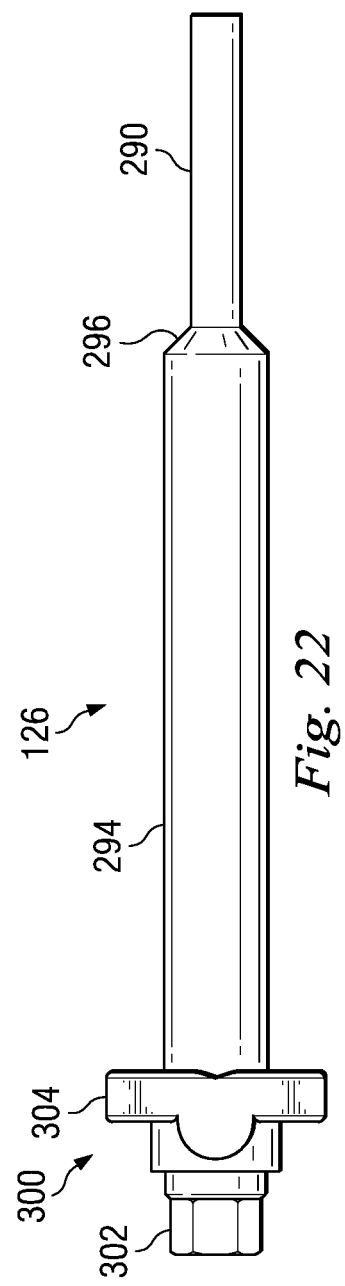
FIG. 22 is a diagrammatic top view of the engagement shaft of FIG. 21.

Referring again to FIG. 7B, the driver 100 also includes the engagement shaft 126. Further details of the engagement shaft 126 are shown in FIGS. 21 and 22. FIG. 21 is a diagrammatic side view of the engagement shaft 126. FIG. 22 is a diagrammatic top view of the engagement shaft 126. Referring now to FIGS. 7B, 21, and 22, the engagement shaft 126 includes a proximal portion 290. The proximal portion 290 is sized and shaped to mate with the opening 206 of the distal portion 204 of the main shaft 108. In that regard, in the illustrated embodiment the proximal portion 290 has a diameter 292 that is substantially equal to or less than the diameter of the opening 206. The proximal portion 290 expands into a central portion 294 of the engagement shaft 126 via a taper 296. The central portion 294 has a diameter 298 that is adapted to allow the engagement shaft 126 to translate at least partially within the opening 286 of the sleeve 118. Thus, the diameter 298 of the central portion 294 of the engagement shaft 126 is substantially equal to or less than the smallest diameter of the opening 286.

The engagement shaft 126 also includes a distal portion 300. The distal portion 300 is adapted to engage the fixation device 30. In that regard, the distal portion 300 includes a driver portion 302 adapted to mate with the engagement mechanism 40 of the fixation device 30 (see FIG. 3). In the illustrated embodiment, the driver portion 302 is illustrated as a hex-shaped driver for engagement with a hex-shaped recess of the fixation device 30. However, as described with respect to the engagement mechanism 40 of the fixation device 30, the driver portion 302 may take the form of numerous other structures, such as a flathead screwdriver, a Phillips-head screwdriver, any other geometrical projections, any other type of projection for mating with a recess of a fixation device, and combinations thereof. Further, in other embodiments, the driver portion 302 is a recess for mating with a projection of the fixation device.

In the illustrated embodiment, the distal portion 300 also includes a flange member 304. The flange member 304 extends beyond the central portion 294, as best seen in FIG. 22. The flange member 304 is adapted to mate with the opening 42 of the fixation device 30. The flange member 304 engages the walls of the opening 42 to help prevent unwanted rotation of the fixation device 30 during engagement with the driver 100. For example, in the illustrated embodiment the flange member 304 may be engaged with the walls of the opening 42 to prevent unwanted rotation of the fixation device 30 during engagement of the threaded portion 124 of the sleeve 118 to the threaded recesses 44 of the fixation device. Further, the driver portion 302 may be engaged with the engagement mechanism 40 to further prevent unwanted rotation of the fixation device 30 during engagement of the threaded portion 124 to the threaded recesses 44.

Figure 23:
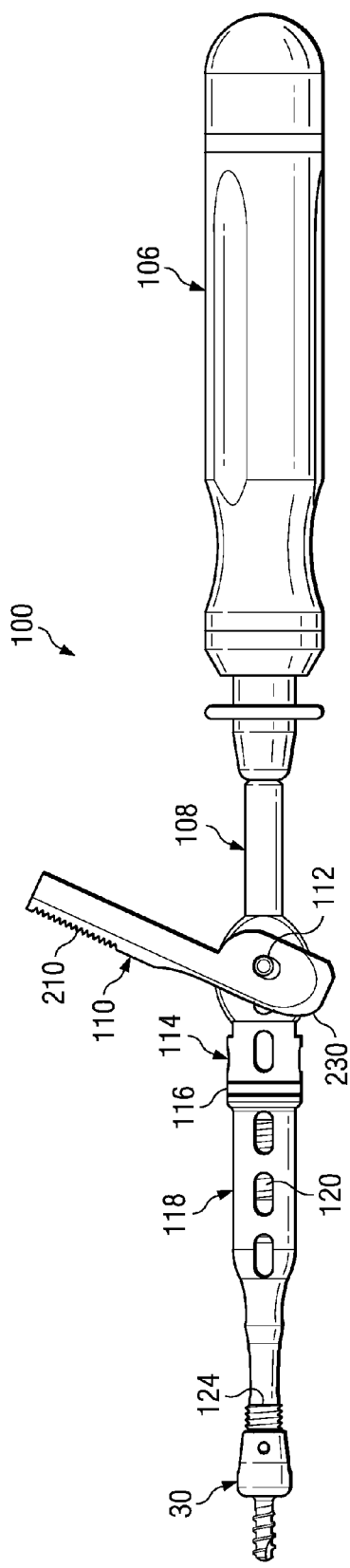
FIG. 23 is a diagrammatic side view of the driver of FIG. 5 in an open and unlocked position.
Figure 24:
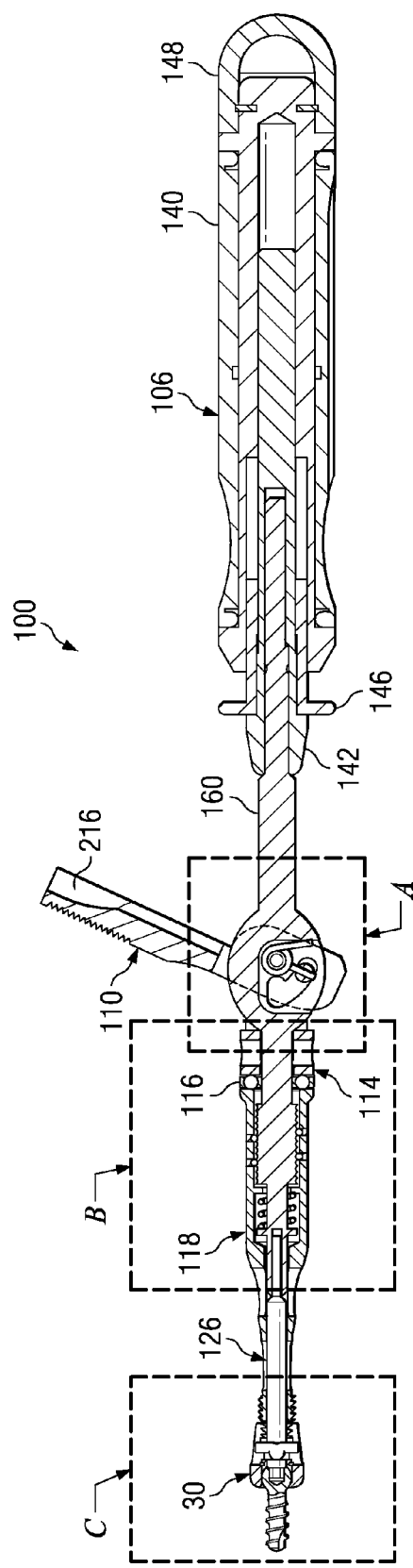
FIG. 24 is a diagrammatic, side cross-sectional view of the driver of FIG. 5 in the open and unlocked position.
Figure 25:
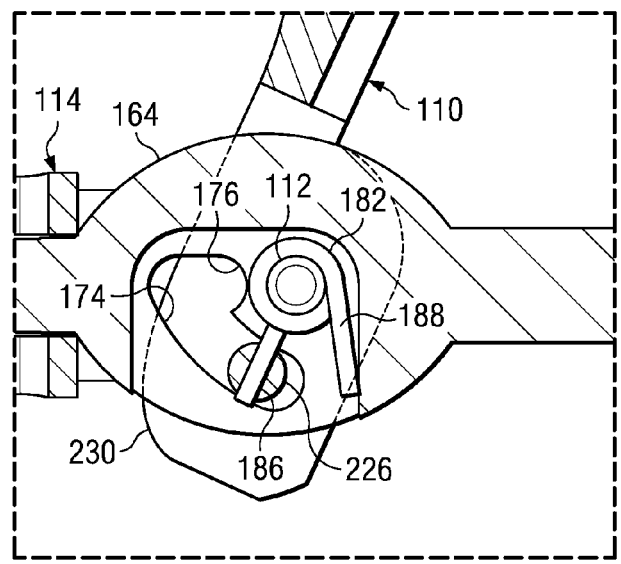
FIG. 25 is an enlarged scale cross-sectional detail view of the circled area "A" in FIG. 24 showing an orientation of the actuator, torsion spring, and main shaft when the driver is in the open and unlocked position.
Figure 26:
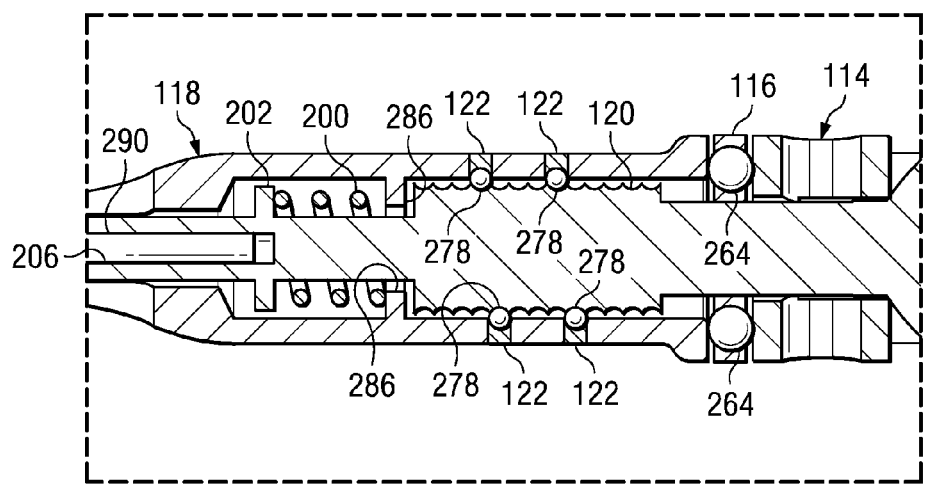
FIG. 26 is an enlarged scale cross-sectional detail view of the circled area "B" in FIG. 24 showing an orientation of the bias spring, balls, and ball threads when the driver is in the open and unlocked position.
Figure 27:
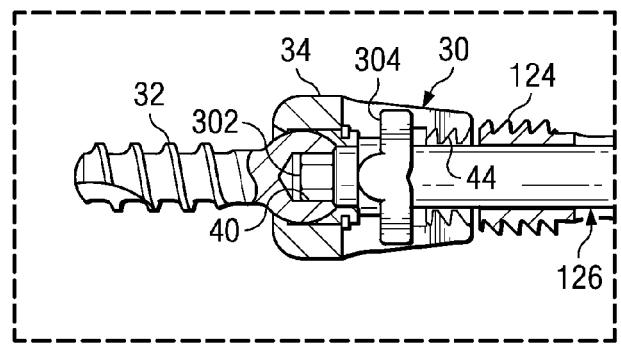
FIG. 27 is an enlarged scale cross-sectional detail view of the circled area "C" in FIG. 24 showing an engagement between the engagement shaft of the driver and a fixation device when the driver is in the open and unlocked position.

Referring now to FIGS. 23-27, shown therein is the driver 100 in an open and unlocked position. FIG. 23 is a diagrammatic side view of the driver 100 in the open and unlocked position. FIG. 24 is a diagrammatic, side cross-sectional view of the driver 100 in the open and unlocked position. FIG. 25 is a diagrammatic, exploded cross-sectional view of a portion of the driver 100 showing an orientation of the actuator 110, the torsion spring 182, and the main shaft 108 when the driver is in the open and unlocked position. FIG. 26 is a diagrammatic, exploded cross-sectional view of a portion of the driver 100 showing an orientation of the spring 200, the balls 278, and the ball thread 120 when the driver is in the open and unlocked position. FIG. 27 is a diagrammatic, exploded cross-sectional view of a portion of the driver 100 showing the engagement between the engagement shaft 126 of the driver and the fixation device 30 when the driver is in the open and unlocked position.

As shown, in the open and unlocked position the gripping portion 210 of the actuator 110 is lifted away from the main shaft 108 so that the bushing 114 is not urged distally by the cam surface 230. Referring more specifically to FIG. 25, the spring 182 assists in biasing the actuator 110 towards the open position. The lead 186 of the spring 182 urges the cross member 226 of the actuator 110 towards the lower portion of the opening 274 away from the detent 276. By urging the cross member 226 towards the lower portion of the opening 274 the gripping portion 210 of the actuator 110 is urged away from the main shaft 108. Referring more specifically to FIG. 26, the spring 200 also assists in biasing the actuator 110 towards the open position. In that regard, the spring 200 interfaces with the annular flange 202 of the main shaft 108 and the flanges 286 of the sleeve 118 to urge the annular flange 202 away from the flanges 286. In doing so, the spring 200 urges the sleeve 118 proximally relative to the main shaft 108. The sleeve 118, in turn, urges the thrust bearing 116 and bushing 114 proximally, which helps maintain the actuator 110 in the open position. Also, the ball bearings 278 engage the ball thread 120 and the surface plugs 122 in the open position, as shown.

Referring more specifically to FIG. 27, the engagement shaft 126 can mate with the engagement mechanism 40 of the fixation device 30 when the driver is in the open and unlocked position. As shown, in the illustrated embodiment the hex-shaped driver portion 302 of the engagement shaft 126 engages the hex-shaped recess of the engagement mechanism 40. Further, the flange member 304 extends within the opening 42 of the fixation device 30. Together, driver portion 302 and the flange member 304 will serve to hold the fixation device 30 in a fixed position relative to the engagement shaft 126 so that the threaded portion 124 of the sleeve 118 can be threaded into the threaded recesses 44 of the fixation device. However, in the open position the threaded portion 124 of the sleeve 118 does not substantially engage the threaded recesses 44 of the fixation device 30, as shown. In some embodiments, the threaded portion 124 of the sleeve 118 may be positioned such that a first thread of the threaded portion 124 engages a first recess of the threaded recesses 44 while in the open position.

Figure 30:
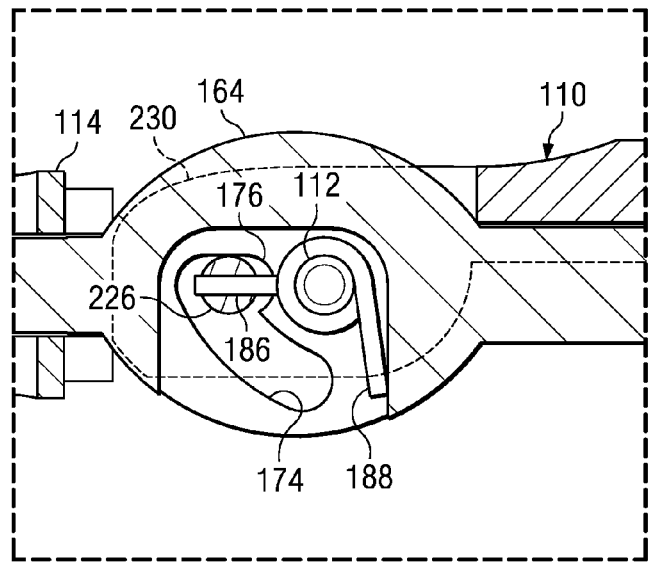
FIG. 30 is an enlarged scale cross-sectional detail view of the circled area "D" in FIG. 29 showing an orientation of the actuator, torsion spring, and main shaft when the driver is in the closed and unlocked position.
Figure 31:
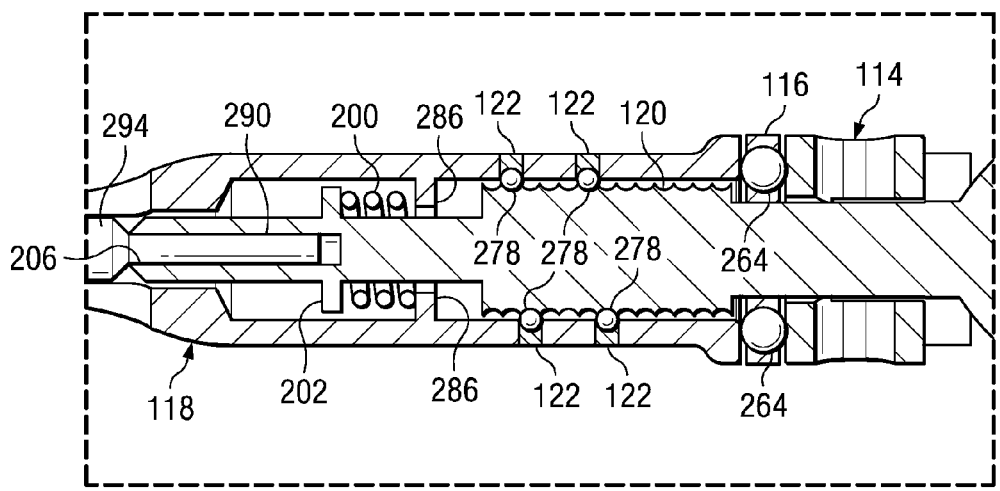
FIG. 31 is an enlarged scale cross-sectional detail view of the circled area "E" in FIG. 29 showing an orientation of the bias spring, balls, and ball threads when the driver is in the closed and unlocked position.
Figure 32:
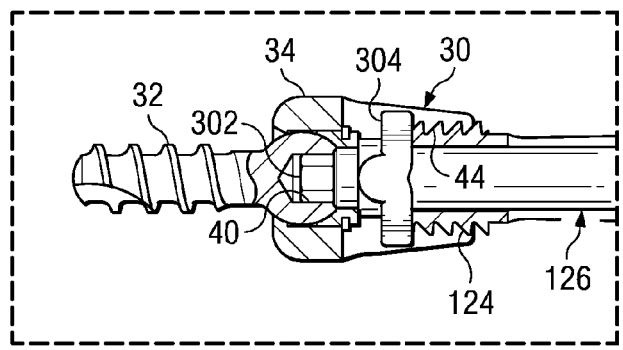
FIG. 32 is an enlarged scale cross-sectional detail view of the circled area "F" in FIG. 29 showing an engagement between the engagement shaft of the driver and a fixation device when the driver is in the closed and unlocked position.

Referring now to FIGS. 28-32, shown therein is the driver 100 in a closed and unlocked position. FIG. 28 is a diagrammatic side view of the driver 100 in the closed and unlocked position. FIG. 29 is a diagrammatic, side cross-sectional view of the driver 100 in the closed and unlocked position. FIG. 30 is a diagrammatic, exploded cross-sectional view of a portion of the driver 100 showing an orientation of the actuator 110, the torsion spring 182, and the main shaft 108 when the driver is in the closed and unlocked position. FIG. 31 is a diagrammatic, exploded cross-sectional view of a portion of the driver 100 showing an orientation of the spring 200, the balls 278, and the ball thread 120 when the driver is in the closed and unlocked position. FIG. 32 is a diagrammatic, exploded cross-sectional view of a portion of the driver 100 showing the engagement between the engagement shaft 126 and the fixation device 30 when the driver is in the closed and unlocked position.

As shown, in the closed and unlocked position the gripping portion 210 of the actuator 110 is positioned adjacent the main shaft 108 so that the bushing 114 is urged distally by the cam surface 230. Referring more specifically to FIG. 30, as the actuator 110 is closed the cross member 226 travels along the opening 274 towards the detent 276. As the cross member 226 travels along the opening 274, the spring 182 is tensioned by the lead 186 of the spring 182 moving with the cross member 226. The tension in the spring 182 is overcome by the downward force imparted on the gripping portion 210 by the user. As the actuator 110 is moved from an open position to the closed position, the increased thickness of the actuator 110 between the pivot rod 112 and the cam surface 230 forces the bushing 114 to translate distally. In the closed position, the recess 216 at least partially mates with the engagement portion 142 of the handle 106. In that regard, in the closed position none of the components of the driver 100 extend radially from longitudinal axis L beyond the profile of the handle 106.

Referring more specifically to FIG. 31, as the bushing 114 is urged distally by the actuator 110, the thrust bearing 116 and the sleeve 118 are also urged distally. As the sleeve 118 is urged distally the ball bearings 278 interact with the ball thread 120 and the plugs 122 to cause the sleeve 118 to rotate. As shown, the ball bearings 278 travel along the ball thread distally as the sleeve 118 is forced distally. As the sleeve 118 rotates and translates distally, the spring 200 is compressed between the annular flange 202 of the main shaft 108 and the flanges 286 of the sleeve 118. Referring more specifically to FIG. 32, also as the sleeve 118 rotates and translates distally, the threaded portion 124 of the sleeve is threaded into the threaded recesses 44 of the fixation device 30. The hex-shaped driver portion 302 and the flange member 304 prevent unwanted rotation of the fixation device relative to the driver 100 so that the threaded portion 124 of the sleeve 118 can be threaded into the threaded recesses 44 of the fixation device 30. In some embodiments, the threaded portion 124 is adapted to thread into the recesses 44 of the fixation device 30 until the threaded portion contacts the flange member 304 of the engagement shaft 126. In some embodiments, the threaded portion 124 may be adapted to thread into the recesses 44 a predetermined distance or a certain number of rotations.

Figure 33:
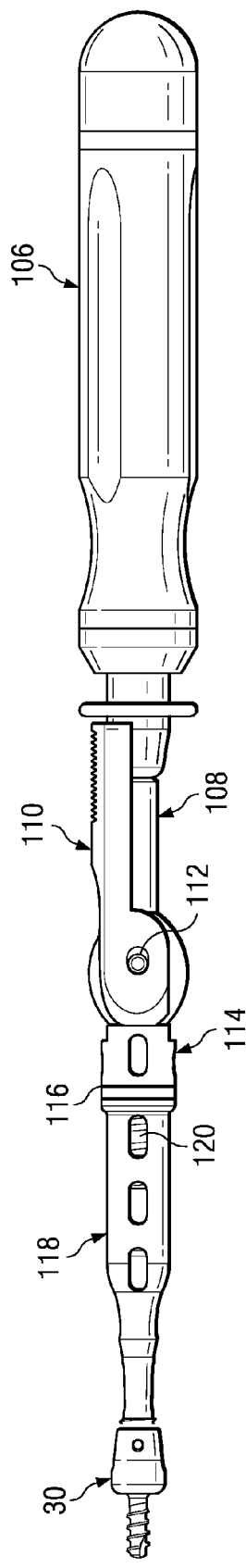
FIG. 33 is a diagrammatic side view of the driver of FIG. 5 in a closed and locked position.
Figure 34:
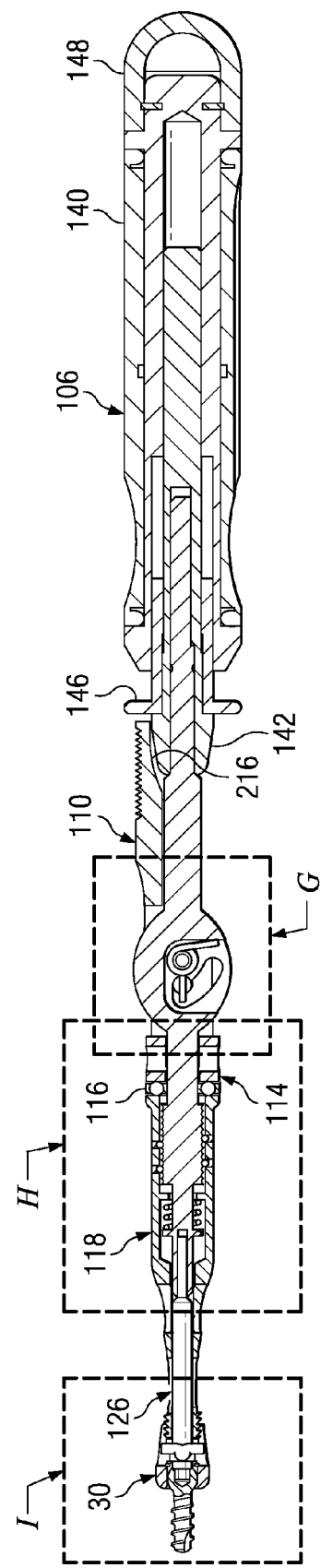
FIG. 34 is a diagrammatic, side cross-sectional view of the driver of FIG. 5 in the closed and locked position.
Figure 35:
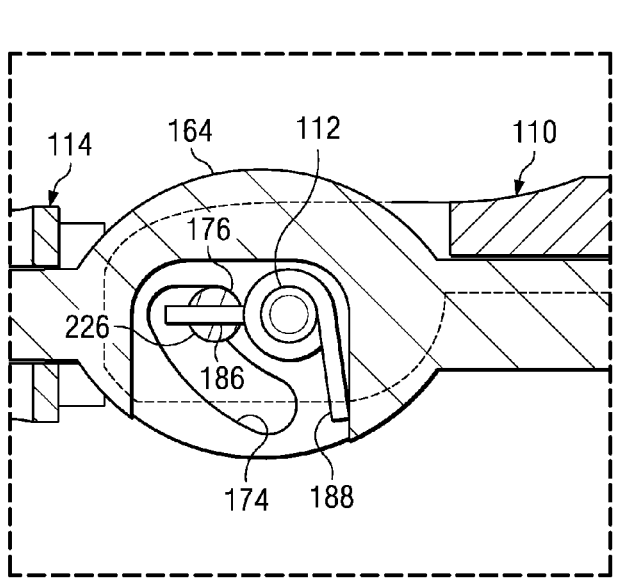
FIG. 35 is an enlarged scale cross-sectional detail view of the circled area "G" in FIG. 34 showing an orientation of the actuator, torsion spring, and main shaft when the driver is in the closed and locked position.
Figure 36:
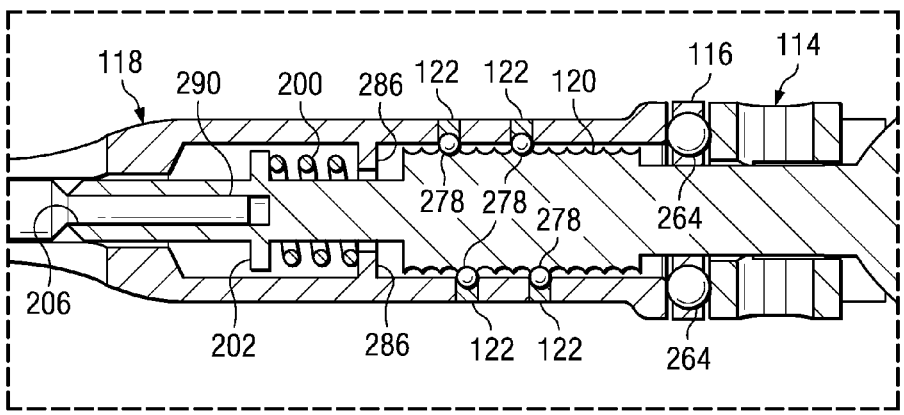
FIG. 36 is an enlarged scale cross-sectional detail view of the circled area "H" in FIG. 34 showing an orientation of the bias spring, balls, and ball threads when the driver is in the closed and locked position.
Figure 37:
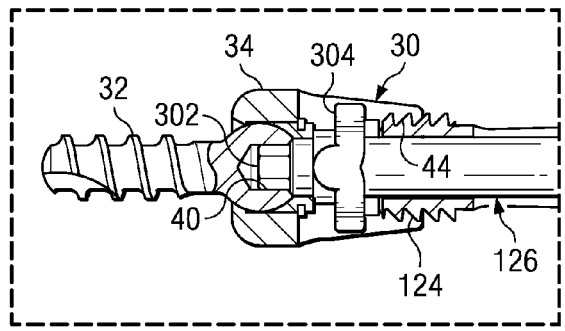
FIG. 37 is an enlarged scale cross-sectional detail view of the circled area "I" in FIG. 34 showing an engagement between the engagement shaft of the driver and a fixation device when the driver is in the closed and locked position.

Referring now to FIGS. 33-37, shown therein is the driver 100 in a closed and locked position. FIG. 33 is a diagrammatic side view of the driver 100 in the closed and locked position. FIG. 34 is a diagrammatic, side cross-sectional view of the driver 100 in the closed and locked position. FIG. 35 is a diagrammatic, exploded cross-sectional view of a portion of the driver 100 showing an orientation of the actuator 110, the torsion spring 182, and the main shaft 108 when the driver is in the closed and locked position. FIG. 36 is a diagrammatic, exploded cross-sectional view of a portion of the driver 100 showing an orientation of the spring 200, the balls 278, and the ball thread 120 when the driver is in the closed and locked position. FIG. 37 is a diagrammatic, exploded cross-sectional view of a portion of the driver 100 showing the engagement between the engagement shaft 126 and the fixation device 30 when the driver is in the closed and locked position.

Generally, the orientation of the components of the driver 100 in the closed and locked position is similar to orientation in the closed and unlocked position. However, as shown the actuator 110 has been translated proximally along the longitudinal axis L of the driver 100 to lock the actuator in the closed position. In that regard and referring more specifically to FIG. 35, translating the actuator 110 proximally when in the closed position causes the cross member 226 to move into the detent 276 of the opening 274. Being positioned within the detent 276 prevents the cross member 226 from traveling along the opening 274 back towards an open position despite the tension on the springs 182 and 200 urging the actuator 110 towards the open position. In this manner, the driver 100 is locked into the closed position. In other embodiments, the driver 100 may be locked into the closed position by engaging a pin within an opening, using a stop, and/or other structures. The locking mechanism may or may not require translation of the actuator 110. Numerous other mechanisms may be utilized for locking the actuator 110 and the driver 100 in the closed position as would be apparent to one skilled in the art. Further, in some embodiments the springs 182 and 200 may bias the driver 100 towards a closed position rather than an open position.

Referring more specifically to FIG. 36, as the actuator 110 travels proximally the bushing 114, the thrust bearing 116, and the sleeve 118 are permitted to travel proximally as well. In particular, the spring 200 urges the sleeve 118 proximally, which, in turn, urges the thrust bearing 116 and the bushing 114 proximally along the main shaft 108. In that regard, as the sleeve 118 is urged proximally the ball bearings 278 interact with the ball thread 120 and the plugs 122 to cause the sleeve 118 to rotate. As shown, the ball bearings 278 travel along the ball thread proximally as the sleeve 118 is forced proximally by the spring 200. Referring more specifically to FIG. 37, in the illustrated embodiment as the sleeve 118 rotates and translates proximally, the threaded portion 124 of the sleeve is partially unthreaded from the threaded recesses 44 of the fixation device 30. In other embodiments, the locking mechanism used to secure the driver 100 in the locked position may not require partial unthreading of the sleeve 118.

Figure 38:
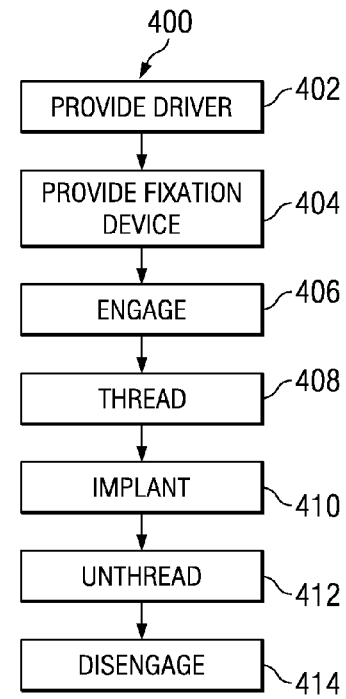
FIG. 38 is a block diagram of a method according to one embodiment of the present disclosure for using a driver.

Referring now to FIG. 38, shown therein is a block diagram of a method 400 according to one embodiment of the present disclosure. The method 400 begins at step 402 where a driver is provided. The driver is adapted to threadingly engage a fixation device. The driver may include an actuator that allows the driver to threadingly engage the fixation device in a single motion. In some embodiments, the driver is substantially similar to the driver 100 described above. The method continues to step 404 where a fixation device is provided. The fixation device includes a threaded area for engagement with the driver. In some embodiments, the fixation device may be a multi-axial screw. Further, in some embodiments the fixation device may be substantially similar to the fixation device 30 described above.

The method 400 continues at step 406 where the driver is engaged with the fixation device. In some embodiments, the driver is engaged with the fixation device by the user holding the fixation device to a portion of the driver. In other embodiments, the engagement may be facilitated by mating a projection of the driver with a recess of the fixation device. For example, in at least one embodiment the driver may include a hex-shaped projection adapted to mate with a hex-shaped recess of the fixation device. Numerous other types of mating projections and recesses may be used. In some embodiments, the engagement between the driver and the fixation device may be adapted to prevent unwanted rotation of the fixation device relative to the driver in subsequent steps of the method 400.

The method 400 continues at step 408 with the threading of the driver onto the fixation device. In some embodiments, the threading of the driver onto the fixation device may be accomplished by actuating an actuator that causes a portion of the driver to spin and, thereby, thread onto the fixation device. In some embodiments, the actuator may be a lever that can be actuated by a user. The method 400 continues with step 410 in which the fixation device is implanted into a patient. In some embodiments, the driver may be locked in the threadingly engaged position prior to implanting the fixation device. After the fixation device has been implanted, the method continues at step 412 in which the driver is unthreaded from the fixation device. In some embodiments, the driver may be unthreaded from the fixation device by reversing the motion of the actuator used to thread the driver to the fixation device. The method continues at step 414 in which the driver is then completely disengaged from the fixation device. The method 400 is for exemplary purposes only and is not to be considered limiting in any way. For example, the driver 100 described above may be used in numerous other methods as would be apparent to one skilled in the art.

Figure 39:
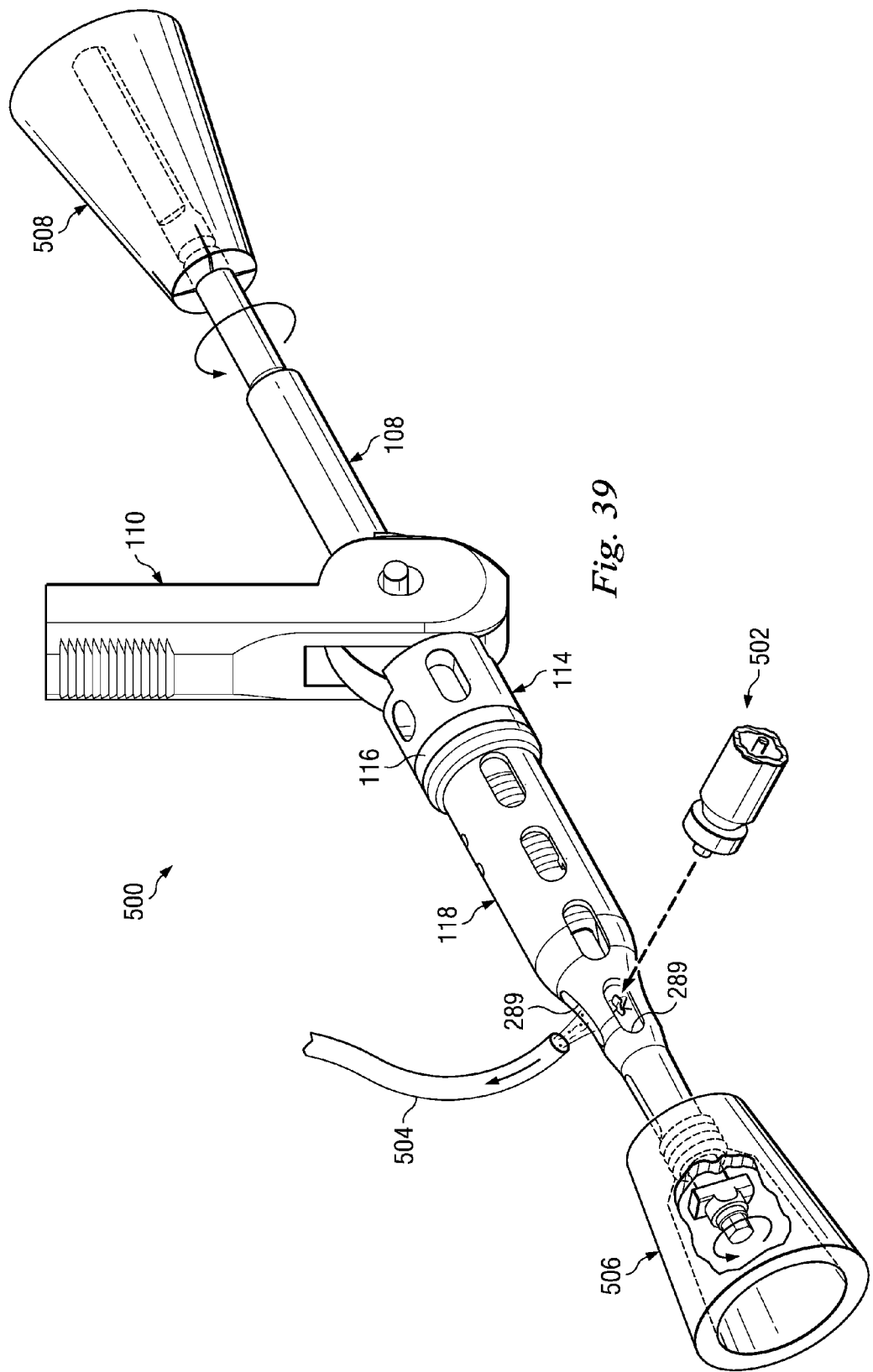
FIG. 39 is a diagrammatic perspective view of a system for assembling a surgical instrument that embodies aspects of the present disclosure.
Figure 40:
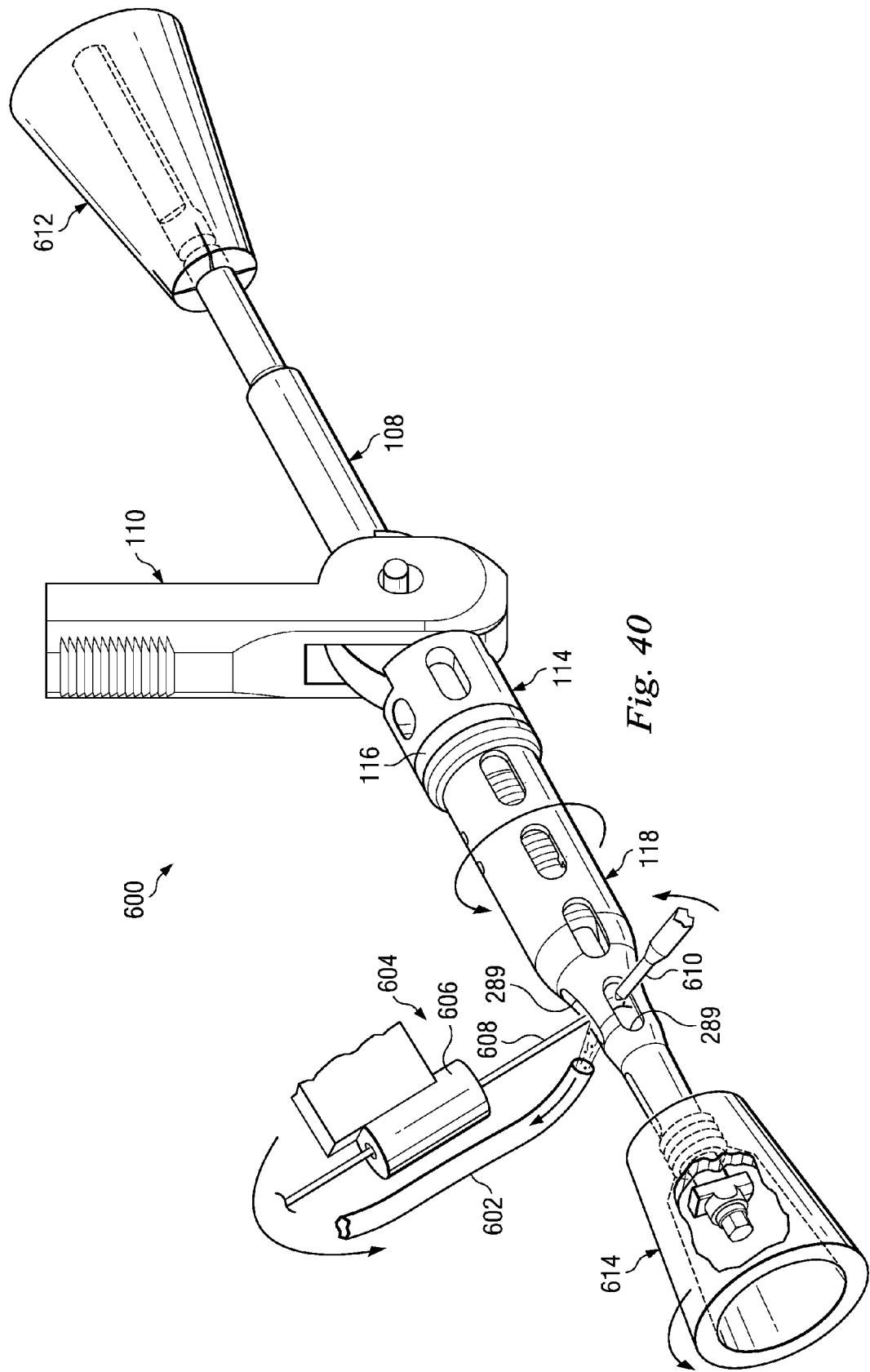
FIG. 40 is a diagrammatic perspective view of a system for assembling a surgical instrument similar to FIG. 39, but showing an alternative embodiment of the present disclosure.

Referring now to FIGS. 39 and 40, shown therein are systems for assembling a surgical instrument that embody aspects of the present disclosure. FIG. 39 is a diagrammatic perspective view of a system 500 for assembling a surgical instrument. FIG. 40 is a diagrammatic perspective view a system 600 for assembling a surgical instrument according to another embodiment. The systems 500 and 600 and related methods will now be described in connection with the assembly of driver 100 for sake of illustration and clarity. However, it is understood that the systems 500 and 600 and related methods may be utilized to connect shaft assemblies of other types of surgical instruments, such as drills, staplers, endoscopic cutters, clip appliers, arthroscopic shavers, electrosurgical cautery devices, and other surgical instruments.

Referring more specifically to FIG. 39, in some embodiments at least one of the openings 289 in the sleeve 118 is utilized by the system 500 as an access window to facilitate welding of the engagement shaft 126 to the main shaft 108. In that regard, at least one of the openings 289 may serve as an access window to the junction of the engagement shaft 126 and the distal portion 204 of the main shaft 108. A welding instrument 502 can then be positioned to utilize the window defined by the opening 289 to access the junction for welding the shafts 126 and 108 together. Welding instrument as used in this context includes any instrument capable of securing the shafts 126 and 108 to one another. Thus, welding instrument includes instruments that may utilize various techniques to secure the shafts 126 and 108 together, such as heat, laser, electron beam, ultrasonic, and other suitable techniques. In the current embodiment, the welding instrument 502 is depicted as a laser welding instrument. The various types of welding instruments and techniques may be used to create spot welds or a circumferential weld between the shafts 126 and 108. As shown, in some embodiments a debris removal line 504, such as a vapor suction line, may utilize another opening 289 providing access to the junction to facilitate removal of debris from the welding process. In other embodiments, the system 500 does not include a debris removal line 504.

In the current embodiment, the system 500 is adapted to provide a circumferentially continuous weld between the shafts 126 and 108. In that regard, the sleeve 118 is held stationary by a collet 506 while the shafts 126 and 108 are rotated by a collet 508. The collet 506 may threadingly or otherwise engage the sleeve 118 to hold it in a fixed position. The collet 508 engages the shaft portion 152 of the proximal portion 150 of the main shaft 108 (see FIGS. 8 and 9) in a manner such that rotation of the collet causes rotation of the main shaft. The engagement shaft 126 may be press-fit or otherwise engaged with the opening 206 of the distal portion 204 of the main shaft 108 such that the engagement shaft and the main shaft rotate together when the collet 508 is rotated. In the current embodiment, as the collet 508 is rotated the shafts 126 and 108 will translate along the longitudinal axis L of the driver 100 due to the ball thread interaction between the main shaft and the sleeve 118. Thus, in the current embodiment, the welding instrument 502 is configured to stay aligned with the junction between the shafts 126 and 108 during rotation and translation of the shafts. In some embodiments, the welding instrument 502 translates along with the shafts 126 and 108. In that regard, the opening 289 of the sleeve 118 utilized by the welding instrument 502 may be elongated to provide sufficient access to the junction between the shafts 126 and 108 as the shafts are translated. In other embodiments, the shafts of the instrument will not translate during rotation and, therefore, the welding instrument can remain stationary as well. As the shafts 126 and 108 are rotated the welding instrument 502 can by utilized to circumferentially weld the shafts together. In some embodiments, the shafts 126 and 108 are rotated at least 360 degrees during a continuous welding procedure to facilitate a circumferentially continuous weld. In other embodiments, the shafts 126 and 108 are rotated during an intermittent welding procedure to create a plurality of spot welds around the circumference of the junction between the shafts.

Referring more specifically to FIG. 40, a system 600 is illustrated. The system 600 utilizes at least one of the openings 289 in the sleeve 118 as an access window to facilitate welding of the engagement shaft 126 to the main shaft 108. In the current embodiment, a debris removal line 602, such as a vapor suction line, also utilizes an opening 289 providing access to the junction to facilitate removal of debris from the welding process. In the current embodiment, a welding instrument 604 utilizes two windows defined by openings 289 to access the junction between the shafts 126 and 108. In that regard, in the current embodiment the welding instrument 604 includes a welding rod feeder 606 for feeding a welding rod 608 via a first opening 289 to the junction of the shafts 126 and 108. The welding instrument 604 also includes a welding tool 610 for welding the shafts 126 and 108 together utilizing the welding rod 608. The welding tool 610 accesses the junction between the shafts 126 and 108 via a second opening 289. In some embodiments, the welding rod 608 and the welding tool 610 access the junction between the shafts 126 and 108 via the same opening 289.

In the current embodiment, the system 600 is adapted to provide a circumferentially continuous weld between the shafts 126 and 108. In that regard, the shafts 126 and 108 are held stationary by a collet 612 while the sleeve 118 is rotated by a collet 614. The collet 612 engages the shaft portion 152 of the proximal portion 150 of the main shaft 108 (see FIGS. 8 and 9). The engagement shaft 126 may be press-fit or otherwise engaged with the opening 206 of the distal portion 204 of the main shaft 108 such that the engagement shaft does not rotate with respect to the main shaft. The collet 614 may threadingly or otherwise engage the sleeve 118 such that the sleeve rotates whenever the collet is rotated. In the current embodiment, as the collet 614 is rotated the sleeve 118 will translate along the longitudinal axis L of the driver 100 due to the ball thread interaction between the sleeve and the main shaft 108. However, the junction between the shafts 126 and 108 will remain in a fixed position. Thus, in the current embodiment, the welding instrument 602 is configured to stay aligned with the openings 289 and the junction between the shafts 126 and 108 during rotation and translation of the sleeve 118. In that regard, in the current embodiment the welding instrument 602 is configured to rotate with the sleeve 118, but not translate. The openings 289 of the sleeve 118 utilized by the welding instrument 602 are elongated to provide sufficient access to the junction between the shafts 126 and 108 as the sleeve 118 translates. As the sleeve 118 and welding instrument 602 are rotated, the welding instrument can circumferentially weld the shafts together. In some embodiments, the sleeve 118 and welding instrument 602 are rotated at least 360 degrees during a continuous welding procedure to facilitate a circumferentially continuous weld of the shafts 126 and 108. In other embodiments, the sleeve 118 and welding instrument 602 are rotated during an intermittent welding procedure to create a plurality of spot welds around the circumference of the junction between the shafts.

The various components of the driver 100 may be formed of any suitable material for use in surgical procedures. For example, but without limitation, the various components of the driver 100 may be formed of any suitable material for use in a surgical procedure including metals (such as cobalt-chromium alloys, titanium alloys, nickel titanium alloys, stainless steel alloys, and other metal alloys); ceramic materials (such as aluminum oxide or alumina, zirconium oxide or zirconia, compact of particulate diamond, pyrolytic carbon, and other ceramics); polymer materials (such as members of the polyaryletherketone (PAEK) family such as polyetheretherketone (PEEK), carbon-reinforced PEEK, or polyetherketoneketone (PEKK); polysulfone; polyetherimide; polyimide; ultra-high molecular weight polyethylene (UHMWPE); cross-linked UHMWPE; and other polymers). Further, the components may each be formed of different materials, permitting metal on metal, metal on ceramic, metal on polymer, ceramic on ceramic, ceramic on polymer, or polymer on polymer constructions.

Also, the various components of the driver, additional surgical tools, implants, and/or fixation devices may be packaged together in a kit. In that regard, several versions of some or all of the various components of the driver may be provided with varying features, such as size, material, shape, etc. Also, the various components of the driver 100 may be modified for use with other implants and fixation devices. For example, in some embodiments the engagement shaft does not include flange member 304 to facilitate use of the driver with a closed multi-axial screw. Numerous other modifications may be made to the components of the driver to facilitate use of the driver with other devices without departing from the scope of the present disclosure. The driver may also be modified for use with computer-guided surgery systems. In that regard, the handle and/or the actuator may be replaced with components adapted to interface with other devices.

Although only a few exemplary embodiments have been described in detail above, those skilled in the art will readily appreciate that many modifications are possible in the exemplary embodiments without materially departing from the novel teachings and advantages of this disclosure. Accordingly, all such modifications and alternative are intended to be included within the scope of the invention as defined in the following claims. Those skilled in the art should also realize that such modifications and equivalent constructions or methods do not depart from the spirit and scope of the present disclosure, and that they may make various changes, substitutions, and alterations herein without departing from the spirit and scope of the present disclosure. It is understood that all spatial references, such as "horizontal," "vertical," "top," "upper," "lower," "bottom," "left," "right," "anterior," "posterior," "superior," "inferior," "upper," and "lower" are for illustrative purposes only and can be varied within the scope of the disclosure. In the claims, means-plus-function clauses are intended to cover the elements described herein as performing the recited function and not only structural equivalents, but also equivalent elements.

What is claimed is:

1. A method for securing a fixation device to a driver for use in a surgical procedure, the method comprising:
   providing a driver comprising:
      an elongated main shaft having a proximal portion, a distal portion, and a longitudinal axis extending therebetween, the distal portion adapted to engage a first portion of the fixation device;
      a handle attached to the proximal portion of the main shaft;
      an actuator movably attached to the main shaft, the actuator moveable between a first position for releasing the fixation device, a second position for engaging the fixation device, and a third position for locking the surgical driver to the fixation device;
      a spring biasing the actuator towards the first position;
      a bushing slidably attached to the main shaft and positioned adjacent the actuator, the bushing adapted to translate along the longitudinal axis when the actuator is moved among the first, second, and third positions;
      a sleeve movably connected via one or more balls to a series of ball threads attached to the main shaft such that the sleeve rotates about the longitudinal axis of the main shaft as it translates along the longitudinal axis, the sleeve comprising a threaded portion for engaging a second portion of the fixation device; and
      a thrust bearing positioned between the sleeve and the bushing to facilitate rotation of the sleeve relative to the bushing;
   engaging a first portion of the driver with the fixation device to limit rotational movement of the fixation device relative to the driver; and
   threadingly engaging a second portion of the driver with the fixation device to limit axial movement of the fixation device relative to the driver, wherein the sleeve member surrounds the elongated shaft;
   wherein engaging the second portion of the driver with the fixation device comprises actuating the actuator of the driver to cause the second portion of the driver to move relative to the first portion of the driver.

2. The method of claim 1 wherein the step of engaging a second portion of the driver with the fixation device includes causing the second portion of the driver to translate axially relative to the first portion of the driver.

3. The method of claim 2 wherein the step of engaging a second portion of the driver with the fixation device includes causing the second portion of the driver to rotate relative to the first portion of the driver.

4. The method of claim 3 wherein causing the second portion of the driver to translate axially relative to the first portion of the driver and causing the second portion of the driver to rotate relative to the first portion of the driver are performed simultaneously.

5. The method of claim 3 wherein engaging the first portion of the driver with the fixation device comprises creating an axial overlap between the fixation device and the first portion of the driver.

6. The method of claim 5 wherein creating the axial overlap comprises mating the driving projection of the first portion of the driver with the driving recess of the fixation device.

7. The method of claim 1 wherein engaging the second portion of the driver with the fixation device further comprises creating relative axial movement between the second portion of the driver and the fixation device.

8. The method of claim 1 wherein engaging the second portion of the driver with the fixation device further comprises creating relative rotational movement between the second portion of the driver and the fixation device.

9. The method of claim 8 wherein creating relative rotational movement between the second portion of the driver and the fixation device is performed in a manner creating an interlocking relationship between the second portion and the fixation device.

10. The method of claim 9 wherein creating the interlocking relationship between the second portion and the fixation device is performed in a manner creating a threaded interconnection between the series of threads of the distal portion of the sleeve member and the corresponding series of threads of the fixation device.

11. The method of claim 1, wherein actuating the actuator of the driver comprises pivoting the actuator relative to a balance of the driver.

12. The method of claim 1, further comprising selectively locking the actuator in a locked position to hold the second portion of the driver in a fixed relation with respect to the first portion of the driver.

13. The method of claim 1, wherein the step of engaging a first portion of the driver with the fixation device includes causing a projection having a non-circular cross section to engage with a recess having a non-circular cross section.

14. A surgical driver comprising:
   an elongated main shaft having a proximal portion, a distal portion, and a longitudinal axis extending therebetween, the distal portion adapted to engage a first portion of an implant;
   a sleeve movably connected to via one or more balls to a series of ball threads attached to the main shaft, the sleeve surrounds the main shaft such that the sleeve rotates about the longitudinal axis of the main shaft as it translates along the longitudinal axis, the sleeve adapted to threadingly engage a second portion of the implant; and
   an actuator movably attached to the main shaft, the actuator being operative to move the sleeve relative to the main shaft between a first position for engaging the implant and a second position for releasing the implant.

15. The driver of claim 14 wherein the distal portion of the main shaft is adapted to engage the first portion of the implant to limit relative rotational movement between the implant and the driver.

16. The driver of claim 15 wherein the sleeve is adapted to threadingly engage the second portion of the implant to limit relative axial movement between the implant and the driver.

17. The driver of claim 16 wherein the implant is a fixation device.

18. The driver of claim 17 wherein the fixation device is a multi-axial screw.

19. The driver of claim 14 further comprising a locking mechanism for securing the sleeve in the first position.

20. The driver of claim 19 wherein the locking mechanism comprises a recess engageable by the actuator.

21. A surgical driver comprising:
- an elongated main shaft having a proximal portion, a distal portion, and a longitudinal axis extending therebetween, the distal portion adapted to engage a first portion of an implant;
- a sleeve movably connected to the main shaft via one or more balls to a series of ball threads attached to the main shaft, such that the sleeve rotates about the longitudinal axis of the main shaft as it translates along the longitudinal axis, the sleeve adapted to threadingly engage a second portion of the implant; and
- an actuator movably attached to the main shaft, the actuator being operative to move the sleeve relative to the main shaft between a first position for engaging the implant and a second position for releasing the implant, wherein the actuator comprises a thumb lever.

22. The driver of claim 21 further comprising a spring biasing the sleeve towards the second position.

23. The driver of claim 21 further comprising a thrust bearing positioned between the actuator and the sleeve to facilitate rotation of the sleeve about the longitudinal axis.

24. A surgical driver for engaging and implanting a fixation device, the surgical driver comprising:
- an elongated main shaft having a proximal portion, a distal portion, and a longitudinal axis extending therebetween, the distal portion adapted to engage a first portion of the fixation device;
- a handle attached to the proximal portion of the main shaft;
- an actuator movably attached to the main shaft, the actuator moveable between a first position for releasing the fixation device, a second position for engaging the fixation device, and a third position for locking the surgical driver to the fixation device;
- a spring biasing the actuator towards the first position;
- a bushing slidably attached to the main shaft and positioned adjacent the actuator, the bushing adapted to translate along the longitudinal axis when the actuator is moved among the first, second, and third positions;
- a sleeve movably connected via one or more balls to a series of ball threads attached to the main shaft such that the sleeve rotates about the longitudinal axis of the main shaft as it translates along the longitudinal axis, the sleeve comprising a threaded portion for engaging a second portion of the fixation device; and
- a thrust bearing positioned between the sleeve and the bushing to facilitate rotation of the sleeve relative to the bushing.

25. A surgical kit comprising:
- at least one fixation device; and
- a driver comprising:
  - an elongated main shaft having a proximal portion, a distal portion, and a longitudinal axis extending therebetween, the distal portion adapted to engage the at least one fixation device to limit relative rotational movement between the fixation device and the driver;
  - a sleeve movably connected to via one or more balls to a series of ball threads attached to the main shaft, the sleeve surrounds the main shaft, the sleeve adapted to threadingly engage the at least one fixation device to limit relative axial movement between the fixation device and the driver; and
  - an actuator movably attached to the main shaft, the actuator adapted to rotate the sleeve relative to the main shaft between a first position for engaging the fixation device and a second position for releasing the fixation device.

26. The kit of claim 25 wherein the at least one fixation device is a multi-axial screw.

27. The kit of claim 26 wherein the at least one fixation device is an open multi-axial screw.

28. The kit of claim 26 wherein the at least one fixation device is a closed multi-axial screw.

29. The kit of claim 26 further comprising a spinal implant.

30. A surgical procedure comprising:
- providing an implant;
- providing a driver comprising:
  - an elongated main shaft having a proximal portion, a distal portion, and a longitudinal axis extending therebetween, the distal portion adapted to engage a first portion of the fixation device;
  - a handle attached to the proximal portion of the main shaft;
  - an actuator movably attached to the main shaft, the actuator moveable between a first position for releasing the fixation device, a second position for engaging the fixation device, and a third position for locking the surgical driver to the fixation device;
  - a spring biasing the actuator towards the first position;
  - a bushing slidably attached to the main shaft and positioned adjacent the actuator, the bushing adapted to translate along the longitudinal axis when the actuator is moved among the first, second, and third positions;
  - a sleeve movably connected via one or more balls to a series of ball threads attached to the main shaft such that the sleeve rotates about the longitudinal axis of the main shaft as it translates along the longitudinal axis, the sleeve comprising a threaded portion for engaging a second portion of the fixation device; and
  - a thrust bearing positioned between the sleeve and the bushing to facilitate rotation of the sleeve relative to the bushing;
- engaging the driver to the implant; and
- implanting the implant.

31. The surgical procedure of claim 30 wherein engaging the driver to the implant comprises engaging the distal portion of the driver to the implant and engaging the sleeve to the implant.

32. The surgical procedure of claim 31 wherein engaging the sleeve to the implant comprises actuating the actuator.

33. The surgical procedure of claim 32 wherein actuating the actuator comprises pivoting the actuator relative to the balance of the driver.

* * * * *